(12) United States Patent
Rabbani et al.

(10) Patent No.: US 7,713,528 B1
(45) Date of Patent: *May 11, 2010

(54) METHOD FOR IN VIVO DELIVERY OF ACTIVE COMPOUNDS USING REAGENT CONJUGATE

(75) Inventors: Elazar Rabbani, New York, NY (US); Jannis G. Stavrianopoulos, New York, NY (US); Sherry P. Goltz, Belle Harbor, NY (US)

(73) Assignee: Enzo Therapeutics, Inc., Farmingdale, NY (US)

( * ) Notice: This patent issued on a continued prosecution application filed under 37 CFR 1.53(d), and is subject to the twenty year patent term provisions of 35 U.S.C. 154(a)(2).

Subject to any disclaimer, the term of this patent is extended or adjusted under 35 U.S.C. 154(b) by 758 days.

(21) Appl. No.: 08/486,062

(22) Filed: Jun. 7, 1995

Related U.S. Application Data (63) Continuation of application No. 08/019,803, filed on Feb. 18, 1993, now abandoned.

(51) Int. Cl.
*A61K 39/395* (2006.01)
*A61K 51/00* (2006.01)
*A61K 31/70* (2006.01)
*C07K 16/00* (2006.01)
*C07K 16/30* (2006.01)

(52) U.S. Cl. .......... 424/178.1; 424/179.1; 424/1.73; 514/44; 530/387.1; 530/387.7; 530/391.5

(58) Field of Classification Search ........... 424/101, 424/9, 1.11, 178.1; 530/391.3, 391.5, 388.8, 530/230.4; 930/300, 350, 387.1; 435/7.1
See application file for complete search history.

(56) References Cited

U.S. PATENT DOCUMENTS

| | | | |
|---|---|---|---|
| 4,182,750 A | 1/1980 | Sullivan et al. | |
| 4,298,685 A | 11/1981 | Parikh et al. | |
| 4,334,017 A | 6/1982 | Plotkin et al. | |
| 4,358,535 A | 11/1982 | Falkow et al. | |
| 4,376,110 A | 3/1983 | David et al. | |
| 4,376,165 A | 3/1983 | Hornby et al. | |
| 4,400,376 A | 8/1983 | Sanderson et al. | |
| 4,486,539 A | 12/1984 | Ranki et al. | |
| 4,510,244 A | 4/1985 | Parks et al. | |
| 4,556,643 A | 12/1985 | Paau et al. | |
| 4,563,417 A | 1/1986 | Alabarella et al. | |
| 4,563,419 A | 1/1986 | Ranki et al. | |
| 4,622,420 A | 11/1986 | Meares et al. | 562/443 |
| 4,623,627 A | 11/1986 | Huang et al. | |
| 4,687,732 A | 8/1987 | Ward et al. | |
| 4,699,876 A | 10/1987 | Libeskind et al. | |
| 4,707,352 A | 11/1987 | Stavrianopoulos | 424/1.1 |
| 4,711,955 A | 12/1987 | Ward et al. | 536/29 |
| 4,724,202 A | 2/1988 | Dattagupta et al. | |
| 4,731,325 A | 3/1988 | Palva et al. | |
| 4,732,847 A | 3/1988 | Stuart et al. | |
| 4,735,210 A * | 4/1988 | Goldenberg | 128/654 |
| 4,749,647 A | 6/1988 | Thomas et al. | |
| 4,755,458 A | 7/1988 | Rabbani et al. | |
| 4,767,609 A | 8/1988 | Stavrianopoulos | 421/1.1 |
| 4,772,548 A | 9/1988 | Stavrianopoulos | 435/5 |
| 4,795,701 A | 1/1989 | Vary et al. | |
| 446,235 A | 12/1989 | Brakel et al. | |
| 4,894,325 A | 1/1990 | Englehardt et al. | |
| 5,180,815 A | 1/1993 | Masuda et al. | |
| 5,241,060 A | 8/1993 | Engelhardt et al. | 536/27 |
| 5,260,433 A | 11/1993 | Engelhardt et al. | 536/23.1 |
| 5,268,299 A | 12/1993 | Shih et al. | |
| 5,288,609 A | 2/1994 | Engelhardt et al. | |

FOREIGN PATENT DOCUMENTS

| | | | |
|---|---|---|---|
| EP | 0070685 | | 1/1983 |
| EP | 0079139 | | 5/1983 |
| EP | 0128332 | * | 12/1984 |
| EP | 0128332 A1 | | 12/1984 |
| EP | 0139489 | | 5/1985 |

(Continued)

OTHER PUBLICATIONS

Burgess et al. Journal of Cell Biology, Nov. 1990 2129.*

(Continued)

*Primary Examiner*—Christine J Saoud
*Assistant Examiner*—Jon M Lockard
(74) *Attorney, Agent, or Firm*—Ronald C. Fedue, Esq.; Cheryl H. Agris (57) ABSTRACT

This invention relates to novel reagent conjugates and a novel multi-step process for delivering active compounds to target analytes of interest in a patient for diagnostic and therapeutic purposes. According to the process, two novel reagents are bound to each other by linkage of the sequence-specific components they contain. The first reagent, which is comprised of a target recognition component and a first sequence-specific component, is introduced into the patient and allowed to achieve maximal localization on the target cells. The second reagent, which is comprised of an active compound component and a second sequence-specific component is then introduced into the patient, thereby forming a complex with the first reagent via the recognition and binding of the sequence-specific components of the two reagents to form the reagent conjugate of the invention. The active compound component is thereby efficiently and specifically delivered to the target analyte.

14 Claims, 5 Drawing Sheets

FOREIGN PATENT DOCUMENTS

| | | |
|---|---|---|
| EP | 0145356 | 6/1985 |
| EP | 0192168 | 8/1985 |
| EP | 0070687 | 10/1985 |
| EP | 0251494 * | 1/1988 |
| EP | 0251494 A2 | 1/1988 |
| EP | 0305145 | 3/1989 |
| EP | 0063879 | 11/1989 |
| EP | 431523 A2 | 6/1991 |
| EP | 0079373 | 10/1992 |
| GB | 2027031 | 2/1980 |
| GB | 2169403 | 6/1988 |

OTHER PUBLICATIONS

Lazar et al. Molecular and Cellular Biology 1988, 1247 vol. 8 No. 3.*
Tao et al. Journal of Immunology vol. 143, 2595 1989.*
Waldman A. Shinu, vol. 252, 1991 1657.*
Hird et al. Genes and Cancer 1990, 184.*
Morag et al. (1996). Reversibility of biotin-binding by selective modification of tyrosine in avidin. Biochem. Journal 316:193-199.*
Khaw et al. (1979). Specificity of localization of myosin-specific antigen antibody fragments in experimental myocardial infarction. circulation. 60:1527-1531.*
Welt et al. (1987). Monoclonal antibody to an intracellular antigen images human melanoma transplants in nu/ny mice. Proc. Natl. Acad. Sci. USA. 84:4200-4204.*
Wadia et al. (2003). Modulation of cellular function by TAT mediated transduction of full length proteins. Current Protein and Peptide Science. 4:97-104.*
Varga et al., Melanotropin-daunomycin conjugate shows receptor-mediated cytotoxicity in cultured murine melanoma cells, *Nature*, 267:56-58 (May 5, 1977).
Kitao et al., "Concanavalin A as a carrier of daunomycin," *Nature*, 265:81-82 (Jan. 6, 1977).
Primus et al., "Localization of Human GW-39 Tumors in Hamsters by Radiolabeled Heterospecific Antibody to Carcinoembryonic Antigen," *Cancer Research*, 33:2977-2982 (Nov. 1973).
Moshakis et al., *Br. J. Cancer 44*:91-90 (1981).
Urdal et al., "Tumor-associated Ganglio-N-triosylceramide," *The Journal of Biological Chemistry*, 256(21):10509-10516 (Nov. 10, 1980).
Halloran et al., "The preparation of nucleotide-protein conjugates: carbodiimides as coupling agents," *The Journal of Immunology 96*(3): 373-378 (1966).
Manning et al., "A Method for Gene Enrichment Based on The Biotin-Avidin Interaction. Application to the Drosophila Ribosomal RNA," *Biochemistry 16*(7): 1364-1370 (1977).
Gown et al., Lab. *Investigation 52*(1): 25 (1985).
Burgess et al., "Possible dissociation of the heparin-binding and mitogentic actives of heparin-binding (Acidic Fibroblast) growth factor-1 from its receptor-binding activities by site-directed mutagenesis of a single lysine residue," *The Journal of Cell Biology 111*: 2129-2138 (1990).
Lazar et al., "Transforming growth factor : mutation of aspartic acid 47 and leucine 48 results in different biological activities," *Mol. & Cellular Biology 8*(3): 1247-1252 (1988).
Tao et al., *J. of Immunology 143*(8): 2595-2601 (1989).
Gillies et al., "Antigen binding and biological activities of engineered mutant chimeric antibodies with human tumor specificities," *Human Antibodies and Hybridomas 1*(1): 47-54 (1990).
Grunstein et al., "Colony Hybridization," *Methods in Enzymology 68*: 379-469 (1979).
Dunn et al., "Determination of fragment ordering," *Methods in Enzymology 65*: 468-478 (1979).
Dunn et al., "A novel method to map transcripts: evidence for homology between an adenovirus mRNA and discrete multiple regions of the viral genome," *Cell 12*:23-26 (1977).
Southern et al., "Detection of specific sequences among DNA fragments separated by gel electrophoresis," *Journal of Mol. Biol. 98*: 503-517 (1975).

Ranki et al., (1983) "Sandwich Hybridization As A Convenient Method For The Detection of Nucleic Acids in Crude Samples," *Gene 21*: 77-85 (1983).
Ranki et al., 1983 "Nucleic Acid Sandwich Hybridization In Adenvirus Diagnosis," *Current topics in Microbiology and Immunology 104*: 307-318 (1983).
Munns et al., "Antibodies specific for modified nucleosides: an immunochemical approach for the isolation and characterization of nucleic acids," *Progress in Nucleic Research and Molecular Biology 24*: 109-114 (1980).
Huang et al., "Monoclonal Antibody Specific For Double-Stranded DNA: A Non-Radioactive Probe Method for Detection of DNA Hybridization," pp. 7-10 in "Rapid Detection and Identification of Infectious Agents," edited by Kingsbury, et al, Academic Press (1985).
Martinell et al., "Three mouse models of human thalassemia," *J. Proc. Natl. Acad. Sci. USA 78*(8): 5056-5060 (1981).
Long et al., "Expression of Ribosomal DNA Insertions In *Drosophilia melanogaster*," *Cell 18*: 1185-196 (1979).
Kimmel A. R. "A Family of Short, Interspersed Repeat Sequences at the 5's End of a Set of Dictyostellum Single Copy mRNAs," *Cell 16*: 787-796 (1979).
Polsky-Cynkin R. et al., "Use of DNA immbolized on plastic and agarose supports to detected DNA by sandwich hybridization," *Clin. Chem. 31*(9): 1438-1443 (1985).
Langdale et al., "A rapid method of gene detection using DNA bound to Sephacryl," *Gene 36*: 201-210 (1985).
Dahlen et al., "Sensitive detection of genes by sandwich hybridization and time resolved flourometry," *Molecular and Cellular Probes 1*: 159-168 (1987).
Keller G. H. et al., "A sensitive nonisotopic hybridization assay for HIV 1 DNA," *Analytical Biochemistry 177*: 27-32 (1989).
Keller G. H. et al., "DNA Probes, Section 5: Hybridization Formats and Detection Procedures," pp. 198-213 (1989).
Syvanen et al., "Fast quantification of nucleic acid and hybrids by affinity-based hybrid collection," *Nucleic Acids Research 14*(12): 5037-5048 (1986.
Decker et al., "Hybridization assay for quantitative detection of viral nucleic acids; application to human immunodeficiency virus-1 and cytomegalovirus" (1989).
Urdea et al., "A novel method for the rapid detection of specific nucleotide sequences in crude biological samples without blotting or radioactivity; application to the analysis of hepatitis B virus in human serum," *Gene 61*: 253-264 (1987).
Urdea et al., "Application of a Rapid Non-Radioactive Nucleic Acid Analysis System to the Detection of Sexually Transmitted Disease Organisms and Their Associated Microbial Resistances," *Clinical Chemistry 35*(8): 1571-1575 (1989).
Sanchez-Pescador et al., "Rapid chemiluminescent nucleic assays for the detection of TEM-1 beta-lactamase-mediated penicillin resistance in neisseria gonorrhoeae and other bacteria," *J. Clin. Microbiology 26*: 1934-1938 (1988).
Symons, "Nucleic Aid Probes," Chap. 4, pp. 103-131 (1989).
Lovgren, T., et al., "Detection of Lanthanide Chelates by Time-Resolved Fluorescence," Chap. 10 of "Nonisotopic DNA Probe Techniques," edited by Kricka, L., Academic Press (1992).
Piper, "Nucleic Acid Probes,"Chap. 2, pp. 49-50 (1985).
Ballard et al., "Monoclonal murine anti-nucleic acid antibody with double-stranded specificity," *Mol. Imunol. 19*(6): 793-799 (1982).
Kidd et al., "$_1$-Antitrypsin deficiency detection by direct analysis of the mutation in the gene," *Nature 304*: 230-239 (1983).
Varga et al., Melanotropin-daunomycin conjugate shows receptor-mediated cytotoxicity in cultured murine melanoma cells, *Nature*, 267:56-58 (May 5, 1977).
Moshakis et al., *Br. J. Cancer*, 44:91-90 (1981).
Godfrey et al., *Experimental Cell Research*, 135:137-45 (1981).
Trubetskoy et al., "On the Possibility of the Unification of Drug Targeting Systems" *Biochemical Pharmacology*, 36(6):839-842 (1987).
Goodwin et al., *J. Nucl. Med.*, 28:722 (1987).
Goodwin et al., *J. Nucl. Med.*, 28:651 (1987).

Goodwin et al., "Pre-targeted Immunoscintigraphy of Murine Tumors with Indium-111-Labeled Bifunctional Haptens," *J. Nucl. Med.*, 29:226-234 (1988).

Halloran et al., "The Preparation Of Nucleotide-Protein Conjugates: Carbodiimides As Coupling Agents," *J. Immunol.*, 96(3):373-378 (1966).

Manning et al., "A New Method of in situ Hybridization," *Chromosoma*, 53:107-117 (1975).

Politz et al., "Ribonucleic Acid-Protein Cross-Linking in *Escherichia coli* Ribosomes: (4-Azidophenyl)glyoxal, a Novel Heterobifunctional Reagent," *Biochemistry*, 20:378-385 (1981).

Sodja et al., "Gene mapping and gene enrichment by the avidin-biotin interaction: use of cytochrome-c as a polyamine bridge," *Nucleic Acids Res.*, 5:383-401 (1978).

Jones et al., "Bromination of Nucleic Acids and their Derivatives," *Nature*, 183(4675):1603-1605) (Jun. 6, 1959).

Lowe, "The Synthesis of Several 8-Substituted Derivatives of adenosine 5'-Monophosphate to Study the Effect of the Nature of the Spacer Arm in Affinity Chromatography," *Eur. J. Biochem*, 73:265-274 (1977).

Dale et al., "The Synthesis and Enzymatic Polymerization of Nucleotides Containing Mercury: Potential Tools for Nucleic Acid Sequencing and Structural Analysis," *PNAS*, 70(8):2238-2242 (Aug. 1973).

Dale et al., "Conversion of covalently mercurated nucleic acids to tritiated and halogenated derivatives," *Nucleic Acids Res.*, 2(6):915-929 (1975).

Agrawal et al., "Efficient methods for attaching non-radioactive labels to the 5' ends of synthetic oligodeoxyribonucleotides," *Nucleic Acids Research*, 14(15):6227-6245 (1986).

Moi et al., "Copper Chelates as Probes of Biological Systems: Stable Cooper Complexes with a Macrocyclic Bifunctional Chelating Agent," *Analytical Biochemistry*, 148:249-253 (1985).

Gown et al., "Monoclonal Antibodies to a Melanoma-Specific Cytoplasmic Antigen," *Laboratory Investigation*, 52(1):1A (1985).

Jue et al., "Addition of Sulfhydryl Groups to *Escherichia coli* Ribosomes by Protein Modification with 2-Iminothiolane (Methyl 4-Mercaptobutyrimidate)," *Biochemistry*, 17(25):5399-5406 (1978).

Lambert et al., "Disulfide Cross-Linking of *Escherichia coli* Ribosomal Proteins with 2-Iminothiolane (Methyl 4-Mercaptobutyrimidate): Evidence That the Cross-Linked Protein Pairs are Formed in the Intact Ribosomal Subunit," *Biochemistry*, 17(25):5406-5416 (1978).

Carlsson et al., "Protein Thiolation and Reversible Protein-Protein Conjugation: N-Succinimidyl 3-(2-Pyridyldithio)Propionate, A New Heterobifunctional Reagent," *Biochem J.*, 173:723-737 (1978).

Weltman et al., "N-Succinimidyl (4-Iodoacetyl) Aminobenzoate: A New Heterobifunctional Crosslinker," *BioTechniques*, 1:148-152 (Sep./Oct. 1983).

Van der Krol et al., 1988, "Modulation of Eukaryotic Gene expression by Complementary RNA or DNA sequencesBiotechniques" 6: 958-976.

* cited by examiner

FIGURE 1A

1. INTRODUCTION OF THE FIRST REAGENT

FIGURE 1B

2. BINDING OF THE FIRST REAGENT TO THE TARGET ANALYTE

FIGURE 1C

3. INTRODUCTION OF THE SECOND REAGENT

FIGURE 1D

4. FORMATION OF THE REAGENT CONJUGATE

FIGURE 2A

1. INTRODUCTION OF THE FIRST REAGENT

FIGURE 2B

2. BINDING OF THE FIRST REAGENT TO THE TARGET ANALYTE

FIGURE 2C

3. CLEARANCE OF UNBOUND FIRST REAGENT BY ADDITION OF OLIGO-(dC)$_n$ LINKED TO TRANSFERRIN

FIGURE 2D

4. INTRODUCTION OF THE SECOND REAGENT

FIGURE 2E

5. FORMATION OF THE REAGENT CONJUGATE

METHOD FOR IN VIVO DELIVERY OF ACTIVE COMPOUNDS USING REAGENT CONJUGATE

This is a continuation of application Ser. No. 08/019,803, filed on Feb. 18, 1993 now abandoned.

BACKGROUND OF THE INVENTION

1. Field of the Invention

The present invention relates to novel reagents and methods which utilize a universal in vivo delivery system based on the use of polymer: polymer recognition and binding to deliver active compounds to target analytes for diagnostic and therapeutic purposes.

2. Brief Description of the Prior Art

Hormones (Varga, J. M., Asato, N., Lande, S, and Lerner, A. B. (1977) Nature 267: 56-58), lectins (Kitao, T. and Hattori, K. (1977) Nature 265: 81-82), and antibodies are among the reagents that have been employed as delivery agents in a variety of systems developed for the purpose of specifically delivering compounds to in vivo targets for diagnostic or therapeutic purposes. However, monoclonal antibodies are currently preferred. Recognition and delivery of therapeutic or diagnostic reagents using these antibodies has been accomplished through a single-step procedure in which the therapeutic or diagnostic reagent is directly conjugated to the monoclonal antibody. These conjugated monoclonal antibodies do not, however, represent a perfect delivery system. Monoclonal antibodies require a long period of time to reach equilibration with cell surface epitopes in vivo and may require up to several days to achieve optimal binding to a particular tissue (Primus, F. J., Wang, R. H., Goldenberg, D. M., et al. (1973) Cancer Res. 33: 2977-2982; Moshakis, V., McIlhinney, R. A. J., Raghavan, D., et al. (1981) Br. J. Cancer 44: 91-90). Thus, the use of monoclonal antibody delivery systems for radioimaging or therapeutic drug delivery, e.g., radioactively labeled monoclonal antibodies or drug-monoclonal antibody conjugates, may result in damage to untargeted tissues due to their lack of specificity and to the lengthy exposure times required. Clearance of these antibody conjugates may also result in some degree of kidney damage due to the large excess of these reagents that must be employed in order to achieve optimal results. In addition, the long equilibration period required for optimal monoclonal antibody binding precludes the use of short-lived radioisotopes in these delivery systems.

A major focus of current research has been to improve targeting of therapeutic or diagnostic reagents to internal target sites, such as to solid tumors or specific organs. One objective of this targeting is to enhance the effectiveness of these conjugated monoclonal antibody reagents by concentrating them at the target site, thereby minimizing their effects on non-target sites. For example, if a reagent is used for therapeutic purposes, such as to treat a solid tumor, improved targeting provides more effective dosing at the target site with fewer non-tumor related side effects. Similarly, where the reagent is a radionuclide used for radioimaging, improved targeting provides enhanced contrast between the target and background areas due to reduced background levels of the radionuclide. Another objective of this research has been to reduce the time required for delivery of the diagnostic or therapeutic reagent to target sites. This has been accomplished using a multi-step procedure in which antibody binding to target sites and reagent delivery are performed in separate steps. The advantage of such a procedure is that the targeting reagent can be allowed to equilibrate for a lengthy period of time without exposing the patient to a potentially harmful reagent. An equilibration period of one or more days will also result in greater specificity and lower backgrounds since excess targeting reagent is likely to be cleared during this period of time.

An example of a multi-step drug delivery procedure which has been used to deliver drugs to cells in vitro is disclosed in an article by Urdai and Hakomori (Urdai, D. L. and Hakomori S. I (1980) J. Biol. Chem. 255: 10509-10516). In this in vitro system, avidin was used as a bridge to link biotinylated, target-specific antibodies to either biotin-drug or biotin-drug-liposome drug carrier reagents.

Godfrey, et al. (Godfrey, W., Doe, B., Wallace, E. F., Bredt, B., and Wofsy, L. (1981) Experimental Cell Research 135: 137-45) also disclose the use of a biotin-avidin bridge to link antibodies to biotinylated drug-carrying liposomes or red blood cell ghosts in a similar multi-step in vitro assay for identifying specific types of cells.

Trubetskoy, et al. (Trubetskoy, V. S., Berdichevsky, V. R., Efremov, E. E., and Torchilin, V. P. (1987) Biochemical Pharmacology 36: 839-842) also recognized that a multi-step procedure results in a more effective delivery of therapeutic or diagnostic reagents to targets. The procedure they propose involves sequential administration of a targeting reagent, i.e., a biotinylated antibody which specifically recognizes and binds to the target site and which accumulates at the targeted tissue, followed by administration of avidin and a biotinylated liposome drug-carrying system which is capable of coupling specifically to the target-bound biotinylated antibody through the avidin bridge. The "bridge" molecules are defined by Trubetskoy as being bifunctional entities in that they have affinity for both the target binding reagent and the drug-carrying reagent. These "bridge" molecules can be "natural polyvalent macromolecules" which are "capable of binding two or more ligands, or synthetic conjugates obtained from molecules possessing two different types of affinty." In this paper the conjugate of the antibody, biotin, and avidin serves as the bridge between the target antigen and the biotinylated liposome, according to Trubetskoy. This system differs from one in which highly specific binding of arrays of like polymer units are used to link targeting and drug-carrying reagents.

In an alternate in vivo delivery system which employs biotin-avidin linkages, Goodwin, et al. (Goodwin, D. A., Meares, C. F., McCall, M. J. and McTigue, M., (1987) J. Nucl. Med. 28: 722) disclose a multi-step procedure wherein a conjugate comprised of streptavidin or avidin, a biotinylated EDTA chelate, and a radioactive metal ($^{111}$In) is used to enhance the localization and delivery of the chelated metal isotope to the liver. This report further demonstrates the feasibility of using a lengthy equilibration period, i.e., 20-24 hours, for equilibration of the targeting entity, avidin, to the target tissue prior to addition of a biotinylated metal chelate complex. This system is further discussed in a subsequent publication by these workers (see, Goodwin, D. A. Meares. C. F., McCall, M. J. McTigue, M., Chaovapong, W., Levy, R. and Starnes, C. (1987) J. Nucl. Med. 28: 561), wherein the authors teach the use of a multi-step in vivo targeting system for mice in which monoclonal antibody-avidin conjugates are pre-equilibrated with target cells in vivo, then subsequently bound to biotinylated radioactive metal chelates prior to radioimaging. This paper also teaches the use of a clearing step with biotinylated human transferrin to remove excess monoclonal antibody-avidin conjugates from the blood. This system is more fully described in Eur. Pat. Pub. No. 0 251 494, published on Jan. 7, 1988, to Goodwin. D. A. Meares, C. and McCall, M. A drawback of this procedure is that high background levels result from the endogenous biotin present in the organism which can result in non-specific binding of the monoclonal antibody-avidin conjugate.

A different multi-step procedure which has been used to image murine tumors was disclosed by Goodwin, et al. (Goodwin, D. A., Meares, C. F., McCall, M. J., McTigue, M. and Chaovapong, W. (1988) J. Nucl. Med. 29: 226-234). In this procedure, antibody to a portion of a metal chelate complex was administered to mice and allowed to passively accumulate in the animal over a period of 20-24 hours. Excess antibody circulating in the blood was then removed by a brief chase with the antigen linked to human transferrin. Radioactively labeled chelate complexes were administered intravenously 1-3 hours before imaging. This procedure represents an improvement over previous radioimaging techniques because it allows for lengthy equilibration periods with a non-radioactive targeting agent, removal of excess targeting reagent, more rapid, specific, and efficient binding of chelated radioactive metals, and shorter periods of exposure to radioactive materials. However, its efficacy is reduced by the loss of antibody-bound chelated radioisotopes, since binding of these antibodies to metal chelates is very weak, resulting in weak signals and high background levels. Moreover, the antibodies are not specifically directed to a single organ, tissue, or cell type, further resulting in non-specific distribution of the radioactive chelate and high background levels.

The use of the above-described delivery systems for therapeutic or diagnostic reagents also presents a health hazard to the patient because high levels of such reagents must be used in these procedures. Thus, there is a need to develop a delivery system which exhibits high specificity for target sites, low background levels, and which also minimizes unnecessary exposure of patients to radioactive ions, or other hazardous materials.

A different type of bridging entity for use in a two-step universal in vitro system for detecting target analytes in a sample is taught in U.S. patent application Ser. No. 08/032,769, filed on Mar. 16, 1993, which is a continuation of U.S. patent application Ser. No. 07/607,787, filed on Oct. 26, 1990, now abandoned, which is a continuation of U.S. patent application Ser. No. 06/922,757, filed on Oct. 24, 1986, now abandoned, which is a Continuation Application of U.S. patent application Ser. No. 491,929, filed on May 5, 1983, now abandoned, both assigned to the instant assignee, which are incorporated by reference herein and made a part thereof. European Patent Application No. 84 10 5028.9-2110 was filed on May 4, 1984, based upon the priority document, U.S. patent application Ser. No. 06/491,929 (filed on May 5, 1983), and published as EP 0 128 332 A1 on Dec. 19, 1984. The European Patent Office issued a Communication under Rule 51(4) EPC on Aug. 20, 1994 indicating its intention to grant a patent thereon. In the first step of the process, a bridging reagent is administered and allowed to achieve binding equilibrium with the target. This reagent has two components. One of the components recognizes the target analyte. The other component is a polynucleotide that specifically recognizes and binds to a component in a second reagent. In the second step of the procedure, a signalling entity is added. This signalling entity also has two components. The polynucleotide component of the signalling entity binds rapidly and specifically to the complementary polynucleotide component of the first reagent, thereby forming a bridge between the two reagents of the invention. The other component of the second reagent is the signal generating compound of the reagent. Binding of the first reagent to the target, followed by binding of the two complementary polynucleotide portions of the first and second reagents to form the bridge, effectively delivers the signal generating compound to the target. In this reference sequence-specific polynucleotide components are used to rapidly and specifically link two reagents in a multi-step process for detection of target analytes in samples.

Thus, there is a need to develop an in vivo delivery system which exhibits high specificity for target sites, low background levels, and which also minimizes unnecessary exposure of patients to radioactive ions, or other hazardous materials. This type of targeted in vivo delivery system would represent a valuable tool for the diagnosis and treatment of a wide variety of disease states.

SUMMARY OF THE INVENTION

The present invention relates to novel reagent conjugates and novel multi-step processes to deliver active compounds to target analytes. The novel reagent conjugates and processes of the invention have broad application in the medical and research field for imaging and for delivery of an unlimited range of compounds to the patient for therapeutic purposes.

The two reagents which make up the reagent conjugate of the invention each consist of two components which may be directly or indirectly linked to each other. The first reagent is comprised of a target recognition component and a first sequence-specific component. The second reagent is comprised of an active compound component and a second sequence-specific component which recognizes and specifically binds to the first sequence-specific component. This second sequence-specific component rapidly finds and attains optimal binding with the first sequence-specific component, thereby linking the two reagents to form the reagent conjugate of the invention.

Each sequence-specific component of the invention consists of an array of covalently linked units which specifically recognizes and binds to a complementary array of similar units comprising the sequence-specific component of the corresponding reagent. These sequence-specific components include, but are not limited to, DNA, DNA-like polymers, RNA, RNA-like polymers, and synthetic polymers with natural or modified ribo- or deoxyribonucleotide bases. The sequence-specific components of the invention may also consist of proteins (especially those which form alpha-helices in solution), leucine zippers, and any other naturally occurring or synthetic polymer that can form specific and stable linkages with other like polymers.

The novel reagent conjugates can be used, for example, to radio-image sites of tumor concentration. Tumor radio-imaging methods are disclosed which employ the novel reagent conjugates of the invention. Application of the instant invention is not limited to the detection of tumors, however, but has broad and unlimited application in diverse areas of medical research and diagnostics to detect any target analyte of interest.

Another aspect of the invention relates to a therapeutic treatment method which comprises the delivery of therapeutic drugs to specific target sites in vivo, e.g. viruses, virus-infected cells, tumor cells, bacterial cells, pathogens, fungi, parasites, and abnormal eukaryotic cells.

Kits for detecting or delivering therapeutic agents to such sites are another aspect of the invention.

In the preferred embodiment, the method of the invention comprises the introduction into the patient of an effective amount of the first reagent, which is comprised of a target recognition component and a first sequence-specific component. The first reagent then equilibrates for an effective amount of time to achieve maximal localization on the target analyte, for example, a cell surface epitope of interest. An effective amount of a second reagent, which is comprised of an active compound component and a second sequence-specific component is then introduced into the patient by an appropriate method. The second sequence-specific component rapidly finds and binds to the first sequence-specific component, thereby delivering the active compound to the target.

In other embodiments of the invention the components of the first and/or second reagents may be administered separately, in a step-wise fashion using a multi-step procedure.

There are several important advantages to be obtained by utilizing the multi-step method of the invention in which two sequence-specific components recognize and bind to each other to link the reagents of the invention. The use of the sequence-specific components to form the reagent conjugate of the invention results in highly specific delivery of the active compound to the target. For applications in which this delivery system forms part of an in vivo detection or imaging system, use of the invention results in superior images and improved detection sensitivity. For therapeutic applications, use of the invention should result in improved efficiency or effectiveness in delivering therapeutic compounds to targets.

These and other objects of the invention will become more fully apparent when the following detailed description of the invention is read in conjunction with the accompanying figures.

DETAILED DESCRIPTION OF THE INVENTION

Figure 1A:
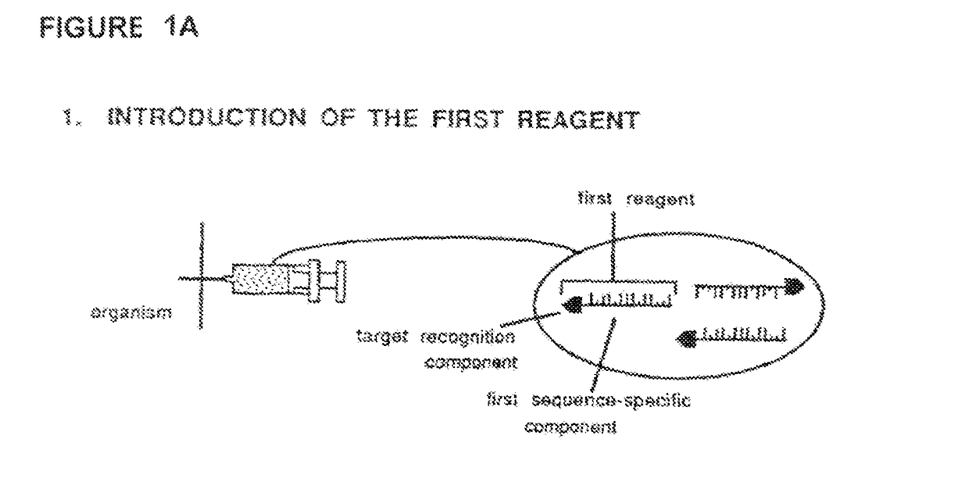
FIG. 1A-1D is a schematic drawing of the delivery of an active compound to a target analyte, in accordance with the invention.
Figure 1B:
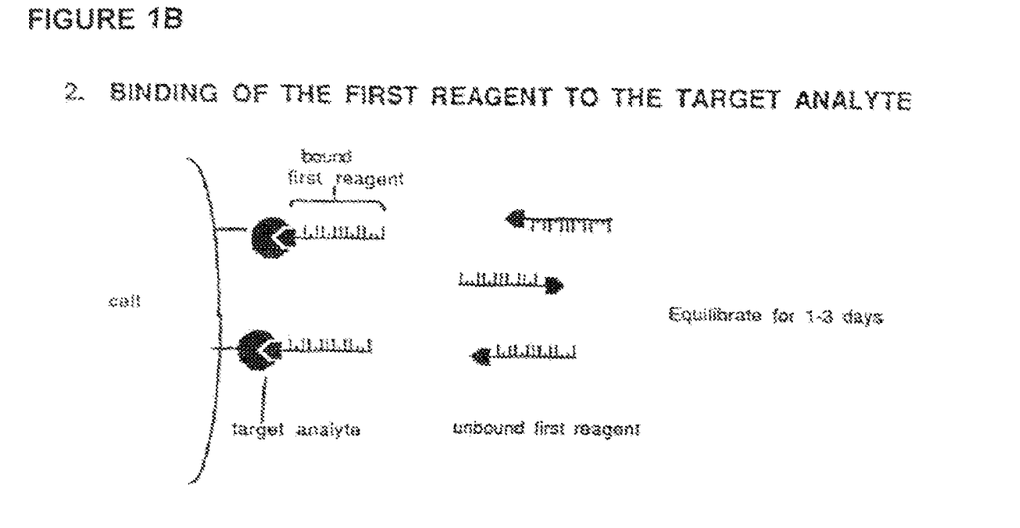
Figure 1C:
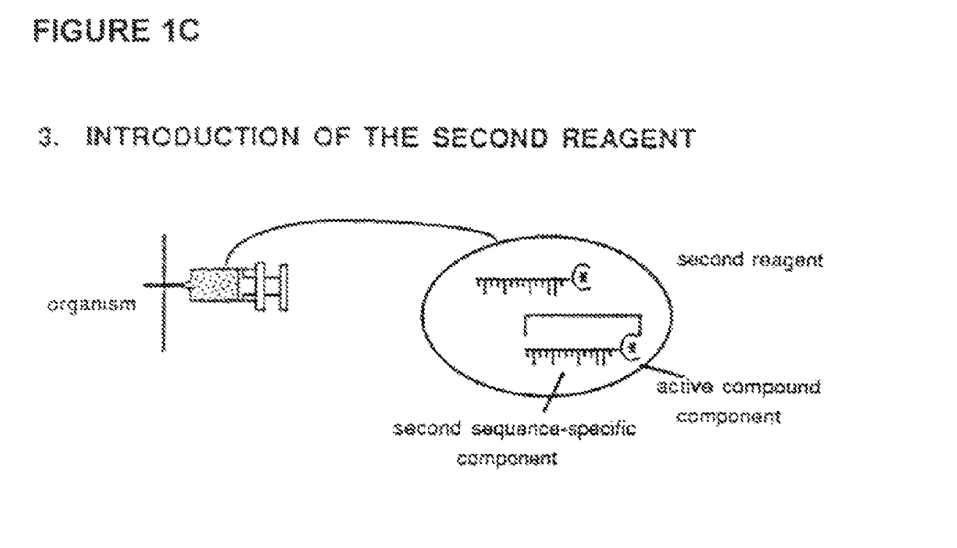
Figure 1D:
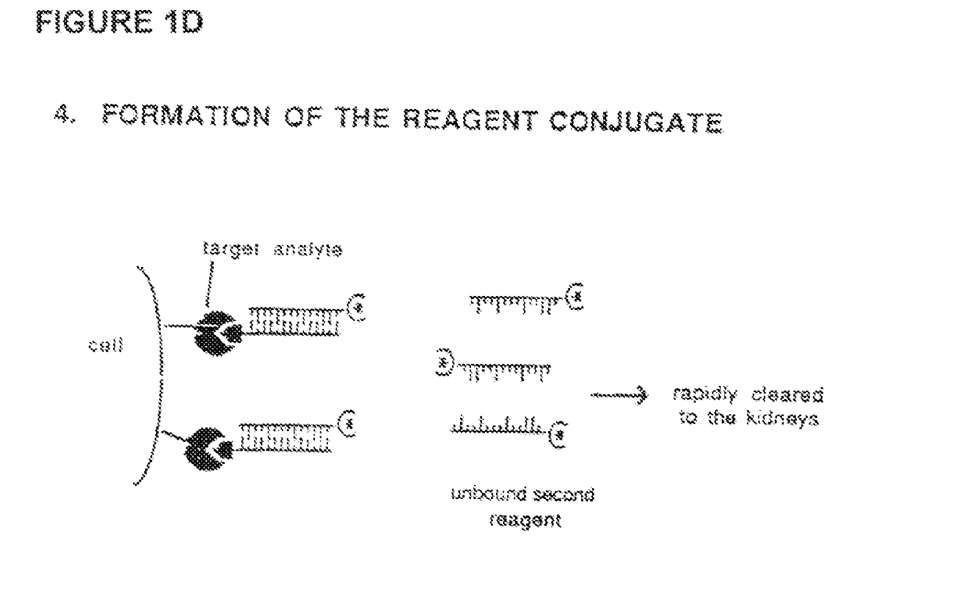

The present invention provides a multi-step procedure (See FIG. 1) for delivering active compounds to target analytes in which a high level of specificity is achieved by the recognition and binding of the sequence-specific components of the two reagents of the invention to each other. This recognition and binding event links the two reagents to form the reagent conjugate of the invention, thereby delivering the active compound to the target analyte.

According to the preferred embodiment of the invention, an effective amount of a first reagent, which is comprised of a target recognition component and a first sequence-specific component, is introduced into a patient by intravenous, subcutaneous, lymphatic, intramuscular, intraperitoneal, or cerebrospinal routes, or by other available methods for introducing macromolecules into an organism. The first reagent then equilibrates for an effective amount of time to achieve maximal localization on the target analyte. An effective amount of a second reagent, which is comprised of an active compound component and a second sequence-specific component, is then introduced into the patient by an appropriate method. The second sequence-specific component rapidly finds and specifically binds to the corresponding first sequence-specific component, which is bound to the first reagent, thereby linking the two reagents to form the reagent conjugate of the invention. Thus, the active compound is delivered with great specificity and efficiency to the target.

In other embodiments of the invention, the components of the first and/or second reagents may be administered separately, in a step-wise fashion using a multi-step procedure. For example, in the case where the components of the first reagent are administered step-wise, the target-recognition component of the first reagent is introduced into the patient and allowed to equilibrate, as in the preferred embodiment. An appropriate quantity of the first sequence-specific component is then added, such that the sequence-specific component is able to find and non-covalently bind to all or most of the target analyte-bound target recognition component, thereby resulting in the formation of the target analyte-bound first reagent in vivo. An effective amount of the second reagent, comprising the second sequence-specific component and the active compound component, may then be administered in a single step and allowed to bind to the target analyte-bound first reagent. If desired, the second reagent may also be added in a step-wise fashion, in which case the second sequence-specific component is administered after the first reagent has been formed, or has reached equilibration with the target, and the second sequence-specific component is allowed to bind to the first sequence-specific component. An effective amount of the active compound component of the second reagent is then added and allowed to bind to the second sequence-specific component which has already been localized to the target analyte-bound first reagent, thereby forming the reagent conjugate of the invention and specifically delivering the active compound to the target site.

In some embodiments of the invention, the individual components of the reagents may be delivered in such a form that they are able to directly bind to each other, i.e., the target recognition component can directly bind to the first sequence-specific component and the active compound component can directly bind to the second sequence-specific component in vivo. For example, the target recognition component may contain a covalently or non-covalently bound avidin moiety and the first sequence-specific component may contain a covalently or non-covalently bound biotin moiety. The binding of the avidin group on the target recognition component to the biotin moiety of the first sequence-specific component will effectively deliver the first sequence-specific component to the target analyte-bound target recognition component, thereby forming the first reagent in vivo. This use of biotin-avidin binding is in direct contrast to previously described delivery systems (see, for example, Goodwin, et al., Journal of Nuclear Medicine (1987) 28:722), where biotin-avidin interactions were used to directly link the target recognition and active compound components of the delivery system.

In other embodiments of the invention, an additional element is required to mediate the binding of the individual components. An example of such an embodiment would be the case where the target recognition component contains a biotin moiety and the first sequence-specific component also contains a biotin moiety. In this case, the target recognition component would be administered and allowed to equilibrate. In a second step, avidin, a biotin-binding protein, would be introduced and allowed to bind to the biotin moiety on the target recognition component. A third step would then consist of introducing the biotinylated first sequence-specific component, which binds to the avidin on the target analyte-bound target-recognition component to form the first reagent. The avidin thus mediates the attachment of the two components of the first reagent in vivo such that they are indirectly bound to each other. As with the first reagent, the components of the second reagent may also be added in a step-wise fashion and may be directly or indirectly linked to each other.

The indirect linkage of the reagent components may also be mediated by interactions between proteins, modified or unmodified, naturally occurring or synthetic nucleic acids, proteins and modified or unmodified, naturally occurring or synthetic nucleic acids, hormones and receptors, small molecular weight organic compounds, metabolites, or any other components that are capable of forming specific and stable linkages.

The term "target recognition component" refers to any substance which is capable of recognizing and binding to the target analytes of the invention. Among the common target recognition components useful according to the invention are antibody fragments, antibody fragment multimers, metabolites, hormones, modified or unmodified, naturally occurring or synthetic nucleic acids or nucleic acid-like polymers. Other target recognition components which can be used in accordance with the invention are naturally occurring or synthetic proteins or other organic polymers with binding specificity and affinity comparable to, or exceeding, that found using antibodies and antibody fragments.

The target recognition component can be used to specifically detect and bind to unique aspects of the analyte. The target analyte of the invention may be comprised of a molecule of small or high molecular weight, a molecular complex. a pathogen, or a biological system, such as a virus, a cell. or a group of cells. For example, target analytes may be comprised of proteins, lipids, carbohydrates, polysaccharides, lipopolysaccharides, protein complexes, and nucleic acids or segments thereof, either single-stranded or double-stranded, which may be found on, or within, a cell, a virus, viral components such as cores or capsids, bacteria of different types, tissue cells, pathogenic or non-pathogenic components of a cell, within the cell or on the cell surface, and the like. Some examples of the types of cells that may be detected in accordance with the invention are bacterial cells, fungal cells, virus-infected cells, abnormal eukaryotic cells, and cancer cells, including those found in tumors, such as melanoma or lymphoma cells, as well as those found in body fluids. Bacteria, either whole cells or fragments thereof, such as cell walls or other recognizable portions, including both gram positive and gram negative bacteria, may also be detected. Fungi and other microorganisms are also detectable, as well as animal cells, e.g. mammalian cells. Among the most common target analyte proteins are the structural proteins, enzymes, immunoglobulins, receptors, or fragments thereof. Among the most common nucleic acids which can be detected are DNA and RNA, including, but not limited to, tRNA, mRNA, rRNA, and the like. Cellular components characteristic of a particular tissue or organ can also be targeted, thereby allowing tissue- or organ-specific delivery of the active compounds of the invention. However, the method of the invention can be used to detect an unlimited range of target analytes. Any protein, lipid, carbohydrate, polysaccharide, polymer, metabolite, or nucleic acid characteristic of a particular tissue, organ, pathogen, or disease state may be detected. In the preferred embodiments of the invention, the target recognition component recognizes cell surface moieties such as proteins, lipids. polysaccharides, lectins or nucleic acids.

The term "active compound component" refers to any substance which is capable of performing a diagnostic or therapeutic function in accordance with the invention. The active compound component is delivered to the patient through the method of the invention either for diagnostic purposes, to detect the presence of the target analytes, or for therapeutic purposes, to treat the patient by delivering therapeutic compounds to specific sites. Examples of active compound components useful in accordance with the invention include, but are not limited to, radioisotopes, complexes of radioisotopes bound to chelator moieties, moieties containing directly or indirectly linked radioactive ions, toxins, cytokines, chemotherapeutic agents, synthetic drugs, differentiation inducers, radio-therapeutic compounds, radio-diagnostic compounds, proteins, hormones, polysaccharides, oligosaccharides, receptors, enzymes, enzyme inhibitors, enzyme substrates, enzyme cofactors, metabolites, vitamins, anti-metabolites, electron dense materials, metal-containing compounds, and naturally occurring or synthetic, modified or unmodified nucleic acids, including those composed of chemically or enzymatically modified bases, sugars or linking groups. Antitumor agents, such as doxorubicin and cisplatin, anti-microbial agents, such as aminoglycosides and antibiotics, anti-fungal agents, anti-viral agents, and anti-parasitic agents are also useful as active compound components of the invention. Liposomes with surface moieties that enable them to recognize and bind to the sequence-specific component of the second reagent may be used to encapsulate any or all of the above-identified active compound components, thereby delivering the active compound components to the target.

The term "sequence-specific component" in accordance with the invention, refers to those polymers which recognize a corresponding unit on another polymer and bind to this unit through the formation of hydrogen bonds, ionic pairs, or through hydrophobic interactions. The first reagent comprises the first sequence-specific component. The second reagent comprises the second sequence-specific component.

Among the most likely sequence-specific components useful according to the method of the invention are DNA, DNA-like polymers, RNA, RNA-like polymers, including but not limited to, modified and unmodified purines and pyrimidines, polypeptides (especially those which form alpha-helices in solution, such as leucine zippers), proteins, as well as synthetic polymers with modified or unmodified nucleotide bases. However, the method of the invention can be applied to any polymer with a given sequence of units which can recognize and specifically bind to a particular sequence of units on another polymer.

A nucleic acid sequence-specific component in accordance with the invention, may comprise any nucleotide sequence, provided that it is long enough to provide stable and specific annealing with a complementary nucleotide sequence under the desired conditions, that it be complementary to the sequence-specific component in the other reagent of the reagent conjugate, and that it be sufficiently different from other nucleotide sequences that may be present so as to avoid the likelihood of binding to non-target sequences. The sequence-specific components useful in accordance with the invention are preferably single-stranded oligonucleotides from about 8 to about 50 bases long, most preferably, from about 8 to about 20 bases in length. This characteristic ensures effective and rapid association between corresponding polymers. A shorter length than that set forth will result in a less effective association between these polymers, while a polymer length greater than that set forth will not result in any additional selectivity of binding. Further, a longer sequence-specific component is more expensive to produce. Other polymer types and lengths are also useful according to the invention. The optimal lengths of these other polymers will depend upon the particular polymer chosen and the specific application for which it will be employed.

In the preferred embodiment, the sequence-specific components are nuclease-resistant oligonucleotides, preferably homopolymers, such as the 2'-modified nucleic acids described in U.S. patent application Ser. No. 08/032,769, filed on Mar. 16, 1993, which is a continuation of U.S. patent application Ser. No. 446,235, filed on Dec. 4, 1989, now abandoned to Brakel, et al, entitled "Modified Nucleotide Compounds." assigned to the instant assignee, the disclosure of which is incorporated by reference herein and made a part hereof. These modified oligonucleotides are more resistant to degradation by nucleases present in serum.

The sequence-specific components may be directly or indirectly linked to the target recognition or active compound components of the two reagents of the invention in vivo or in vitro. Attachment of the two components of each reagent may be direct, by covalent attachment of the two entities. Alternatively, the two components of each reagent may be indirectly joined to each other, such as by non-covalent binding of specific moieties on each component to one or more mediating compounds. They may be introduced into the patient simultaneously with the other components of the reagents either in complexed form, as would be the case when they are joined in vitro, or as individual entities, as when they are joined to the other reagent components in vivo.

The active compound components and target recognition components as defined in this invention are linked by the binding of the first and second sequence-specific components to each other. Alternatively, multiple linkages may be formed in accordance with the invention, such as by the attachment of multiple sequence-specific components to the same target recognition or active compound component, or by the sequential binding or layering of multiple pairs of sequence-specific components to each other to form a linkage between the target recognition component and the active compound component. The formation of multiple linkages may be advantageous with regard to achieving increased sensitivity or specificity for a particular diagnostic or therapeutic effect.

Various methodologies may be used to link the target recognition components and the active compound components of the invention to the first and second sequence-specific components, respectively. In the case where the sequence-specific component is an oligonucleotide, a linker as described in U.S. Pat. Nos. 4,711,955 (issued on Dec. 8, 1987) and 5,328,824 (issued on Jul. 12, 1994), both of which are assigned to Yale University, the disclosures of which are incorporated by reference herein and made a part hereof, maybe used to attach the oligonucleotide to the target recognition or active compound components of the reagent. For example, the linker may be covalently attached to oligonucleotides which have been derivatized such that they contain terminal allylaminouracil groups with accessible amino groups, or terminal thiol groups, as described in Engelhardt et al., U.S. Pat. No. 5,241,060, "Base Moiety-Labeled Nucleotide," issued on Aug. 31, 1994, based on Ser. No. 07/532, 704, filed on Jun. 4, 1990, which is a divisional of Ser. No. 07/140,980, filed Jan. 5, 1988, abandoned, which is a continuation of Ser. No. 06/674,352, filed Nov. 21, 1984, abandoned, which is a continuation application of Ser. No. 06/391, 440, filed Jun. 23, 1982, titled "Modified Nucleotides, Methods of Preparing and Utilizing and Compositions Containing the Same," also abandoned. Also issued in the same aforementioned patent family is Engelhardt et al., U.S. Pat. No. 5,260,433, "Saccharide Specific Binding System Labeled Nucleotides," that issued on Nov. 9, 1993 as a divisional of the aforementioned Ser. No. 07/140,980. Ser. No. 391,440, filed on Jun. 23, 1982, entitled "Modified Nucleotides, Methods of Preparing and Utilizing and Compositions Containing the Same," to D. Engelhardt, et al., now abandoned, which was re-filed as U.S. patent application Ser. No. 674,352 on Nov. 21, 1984, now abandoned, which was re-filed as pending U.S. patent application Ser. No. 140,980 on Jan. 5, 1988, abandoned in favor of continuation application Ser. No. 07/685,982, filed on Apr. 15, 1991. All of the foregoing patent disclosures are incorporated by reference herein and made a part hereof. Thus, in the case where the sequence-specific components of the invention are comprised of oligonucleotides, the methods taught in the above-cited references may be used to attach the target recognition component and the active compound component to their respective sequence-specific components.

Alternatively, oligonucleotides that are attached to linkers which terminate in an N-hydroxysuccinamidyl ester, imidoester, or an imidazolyl carbamate group may be reacted with the amino groups on the target recognition component to yield the first reagent of the invention.

Still another method for attaching an oligonucleotide sequence-specific component to a target recognition or active compound component would be to use an oligonucleotide which is attached to a linker arm that terminates in an amine or a hydrazine group which could then react with the amine groups of the other reagent components.

When the sequence-specific components of the invention are comprised of oligonucleotides and when the above-cited means of attachment are used, the linker arms of the invention are preferably from about 8 to about 30 atoms in length. This length is optimal for separation of the sequence-specific components from either the active compound component or the target recognition component. A linker arm containing fewer atoms could reduce the association between corresponding polymers, interfere with target recognition, or diminish the effectiveness of the active compound component.

Other methods useful in accordance with the invention for covalently attaching polynucleotides to proteins are described in the literature. These methods include carbodiimide cross-linking (Halloran, M. K., J. Immunol. 373 (1966), cross-linking in the presence of formaldehyde (Manning, J. E., et al., Chromosoma 53: 107-117 (1975)), treatment with 4-azidophenyl glyoxal (Politz, S. M., Biochemistry 20: 372-378 (1981), and oxidation of the 2' and 3' hydroxy groups of a polyribonucleotide or a polydeoxyribdnucleotide with a 3'-terminal ribonucleotide, followed by a Schiff's base reaction with the amine groups of a protein and borohydride reduction (Sodja, A., et al., Nucleic Acids Research 5: 383-401 (1978)). Other methods include direct bromination of DNA (Jones, A. S., Nature 183: 1603 (1959) followed by reaction with diaminohexane and coupling via protein carboxyl functions (Lowe, C. R., Eur. J. Biochem 73: 265-274 (1977)), or by mercuration of cytosine moieties (Dale, R. M. K., et al, PNAS 70: 2236-2242(1973)) followed by halogenation (Dale, R. M. K., et al, Nucleic Acids Res. 2: 915-930 (1975)).

According to the preferred embodiment of the invention, the first reagent is comprised of a target recognition component which is an Fab' fragment of an IgG and a first sequence-specific component which is an oligonucleotide with about 8 to about 20 bases. The target recognition component is covalently joined to the first sequence-specific component through an appropriate length linker arm, in accordance with the preferred method of the invention. In this embodiment, the linker, which contains either an iodoacetamide or a bromoacetamide group, is attached to the Fab' fragment on one end and to the 3' terminus of the oligonucleotide on the other end, thereby forming the first reagent of the invention.

Other oligonucleotides, ranging from about 8 to about 50 bases in length may be used as sequence-specific components, in accordance with the invention. These oligonucleotides may be prepared by phosphoramidite chemistry using an automated oligonucleotide synthesizer.

In other embodiments, a 5' terminal amino group may be introduced onto the oligonucleotide sequence-specific component, as described by Agrawal et al. (Agrawal. S., Christodolou, C. and Gait, M. J. (1986) Nucl. Acids. Res. 14: 6227). An activated ester reaction in which the 5' terminal amino group of the oligonucleotide is reacted with a terminal carboxylic acid on a linker may be used to form the first reagent of the invention.

In the preferred embodiment, the first reagent, comprising a complex of the target recognition component and the first sequence-specific component, as described hereinabove, is administered to the patient in a single step, such as by intravenous, subcutaneous, intramuscular, intrabronchial, intrapleural, intraarterial, intraperitoneal, lymphatic, or cerebrospinal routes, or using any other available system for introducing macromolecules into an organism. The dosage at which the first reagent is administered to the patient depends upon the target analyte, as well as upon the particular target recognition and sequence-specific components which are employed.

The equilibration period for the first reagent is that length of time required to achieve maximal localization at the target site. One advantage of the instant invention is that it provides for a delivery system which includes a lengthy equilibration period for the first reagent without unnecessarily exposing the patient to harmful agents for long periods of time. The second reagent can bind quickly and efficiently to the fully equilibrated first reagent, further minimizing the time and amount of patient exposure to potentially harmful active compounds. At the end of the equilibration period, according to a preferred embodiment, the first reagent circulating in the blood may be removed or cleared to prevent it from binding to the second reagent. The method of the invention is not limited to the use of a clearing step. However, background may be reduced, resulting in a clearer image upon radioimaging, when radioimaging is desired in accordance with the invention, if a clearing step is included in the procedure.

Figure 2A:
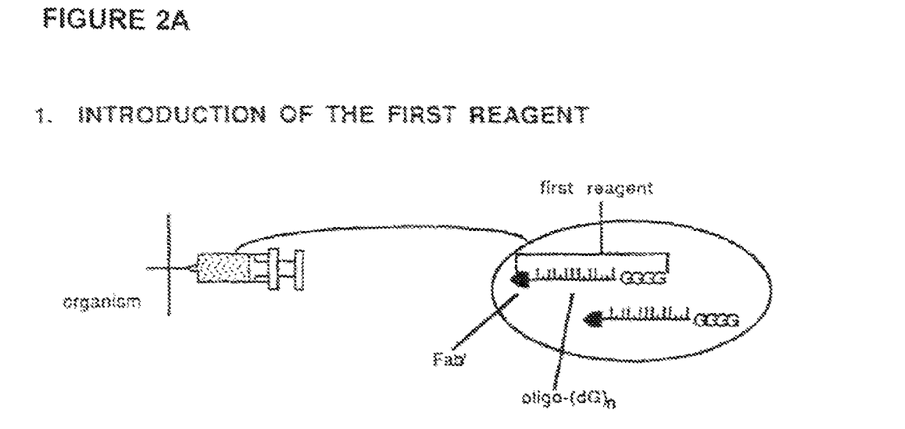
FIGS. 2A-2E is a schematic drawing of the delivery of a chelated radioactive metal ion to targeted cells, including a clearance step (FIG. 2C), in accordance with the invention.
Figure 2B:
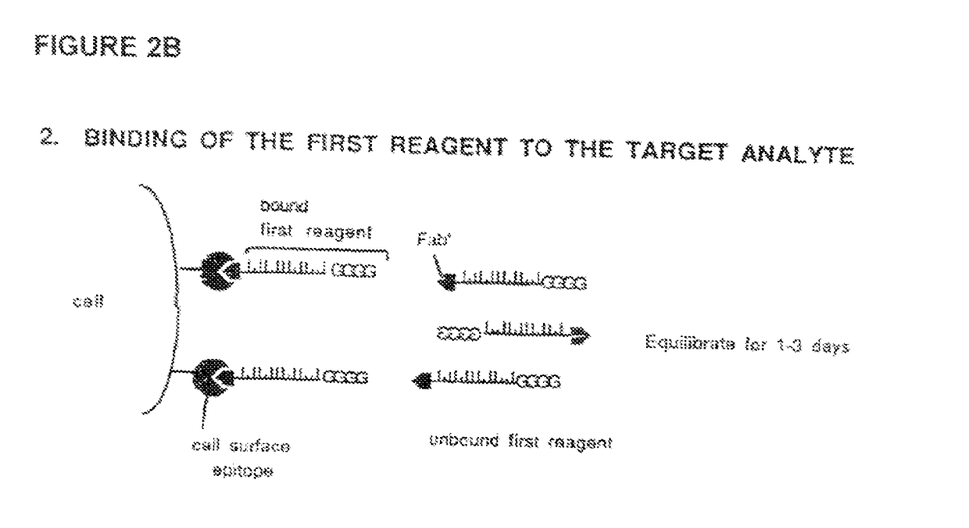
Figure 2C:
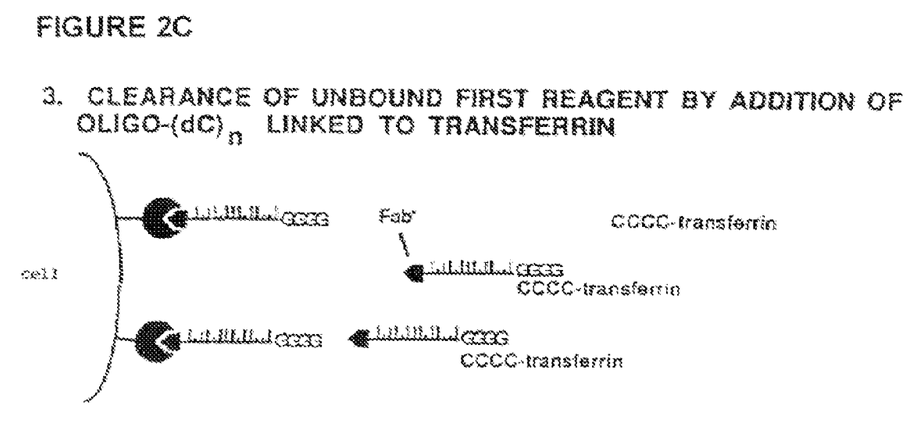
Figure 2D:
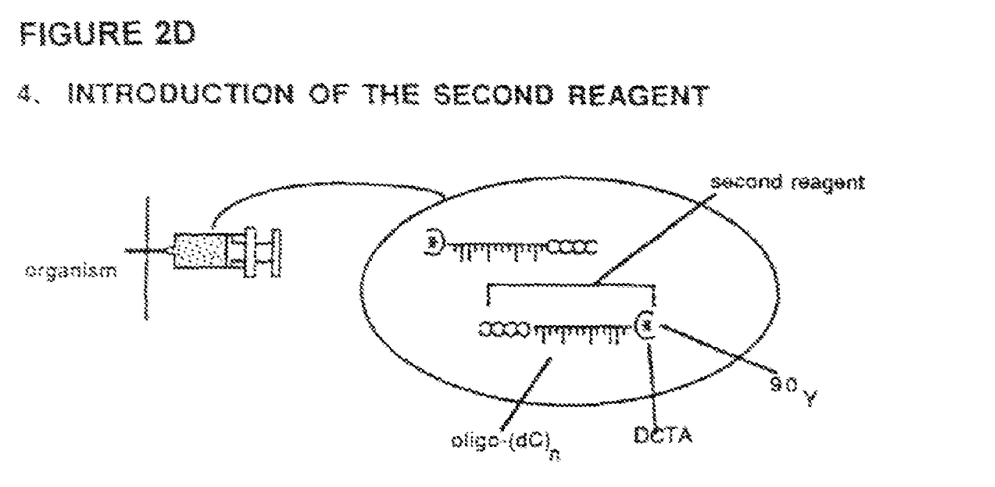
Figure 2E:
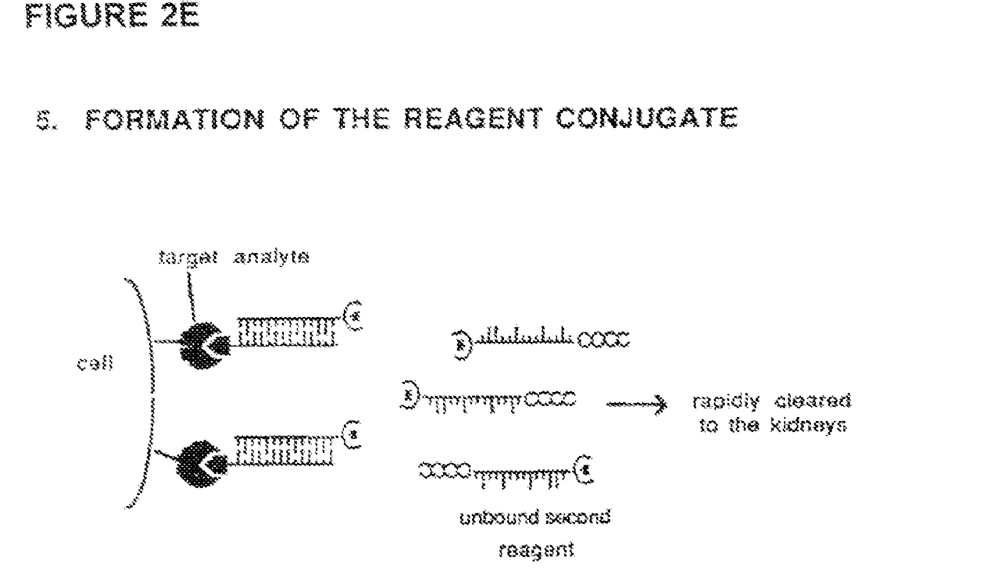

Clearance of excess first reagent from the patient may be effected by a reagent similar to the second reagent. except that the active compound component contained in the second reagent is replaced by a different compound, e.g., human transferrin, according to the preferred embodiment, such that clearance is effected by the binding of the second sequence-specific component in the clearing agent to the first reagent via its complementary sequence-specific component (See FIG. 2). Alternatively, the clearing agent may consist of target analyte or target analyte-like moieties which are attached to transferrin such that the clearing agent binds to the excess. circulating target recognition component of the first reagent. This type of clearing agent is similar to that described by Goodwin, et al., Journal of Nuclear Medicine (1988) 29: 226-234.

In other embodiments of the invention, the target recognition component and the first sequence-specific component may be administered to the patient sequentially, in separate steps such that these components join non-covalently in the patient to form the first reagent. In these cases, adequate time periods are allowed for optimal binding and equilibration of the target recognition component and the target analyte and, subsequently, for binding and equilibration of the first sequence-specific component to the bound target recognition component. Clearance of excess target recognition or first sequence-specific components can be effected using one or more types of clearing agents described in the preferred embodiment of the invention, or any other type or kind of clearing agent useful for the purpose desired. Clearance may be accomplished in a single step, either following the equilibration of the target recognition component, or following the formation of the first reagent, or in multiple steps, following the equilibration of each component type.

After an appropriate period of time has elapsed for equilibration, formation, and clearance of the first reagent, the second reagent is administered to the patient. In the preferred embodiment, the second reagent is comprised of an active compound component and a second sequence-specific binding component, as defined hereinabove, connected by a covalently bound linker arm. In other embodiments, the components of the second reagent are non-covalently attached to one another and may be added as a preformed second reagent. Alternatively, the components of the second reagent may be administered sequentially in a multi-step procedure, wherein the active compound component and the second sequence-specific component are joined in the patient to form the second reagent of the invention. In this embodiment, the second sequence-specific component rapidly finds and binds to the first sequence-specific component which is directly or indirectly attached to the target recognition component, now bound to the target analyte. The active compound component is then added and allowed to bind to the second sequence-specific component, thereby forming the second reagent of the invention and completing the formation of the reagent conjugate.

The formation of the reagent conjugate of the invention is thus dependent upon the presence of the target analyte. The reagent conjugate thereby formed may be used for diagnostic applications, i.e., for imaging, with high sensitivity, specificity, and accuracy, or for therapeutic applications, by virtue of the therapeutic action of the active compounds thereby delivered.

The sequence-specific component of the second reagent in the preferred embodiment is comprised of an oligonucleotide which is complementary to the oligonucleotide which forms the sequence-specific component of the first reagent (See FIG. 2). In the preferred embodiment, this first sequence-specific component is a 2'-modified oligoguanidylate which is about 20 bases in length. The second sequence-specific component is a 2'-modified oligocytidylate which has modified termini that render it resistant to diesterases in the serum. This second sequence-specific component binds rapidly and specifically to the corresponding first sequence-specific component in the first reagent. Modified homopolymers are the preferred sequence-specific components of this invention since they are resistant to nucleolytic degradation and they bind rapidly to complementary oligonucleotides. A reactive amino group is introduced onto the 3' terminus of the oligonucleotide to facilitate covalent attachment of this entity to a suitable linker arm. Derivatization of the oligonucleotide is accomplished using an appropriate type of controlled pore glass bead reaction column. In the preferred embodiment, a linker arm similar to that used to assemble the first reagent, except that it terminates in an N-hydroxy-succinimide group, forms a covalent bond with the derivatized oligonucleotide sequence-specific component of the second reagent. The oligonucleotide is then reacted with a derivatized 1,2-diaminocyclohexanetetraacetate. DCTA, chelator as more fully set forth in U.S. Pat. No. 4,707,352, entitled "Method of Radioactively Labeling Diagnostic and Therapeutic Agents Containing a Chelating Group," issued Nov. 17, 1987; U.S. Pat. No. 4,767,609, entitled "Therapeutic and Diagnostic Processes Using Isotope Transfer to Chelator-Target Recognition Molecule Conjugate," issued on Aug. 30, 1988, and U.S. Pat. No. 4,772,548, entitled "Radioisotopic Assay Using Isotope Transfer to Chelator-Target Recognition Molecule Conjugate," issued on Sep. 20, 1988, all to J. Stavrianopoulos, assigned to the instant assignee, and the disclosures of which are incorporated by reference herein and made a part hereof.

In the preferred embodiment, a radioactive metal ion having a short half-life, such as the beta emitter $^{90}Y$ is used as the active compound component for diagnostic imaging (See FIG. 2). However, other radioactive metal ions may be used, depending upon whether it is desired to image a tissue or organ, or to irradiate and kill undesirable cells or pathogens, for example, viruses, bacteria, or cancerous cells. Additional metal ions, which are also useful in accordance with the invention for diagnostic imaging include, but are not limited to the gamma emitters, $^{111}$In and $^{99m}$Tc, and the positron emitters, $^{49}$Cr, $^{52}$Fe, $^{55}$Co, $^{56}$Mn, $^{61}$Cu, $^{68}$Ga, and $^{90}$Mo. According to the instant invention, these metal ions may be used simultaneously, or individually, in any desired combination, to perform single or multiple radio-imaging assays. Metal ions which are useful for tumor therapy in accordance with the invention may be selected from a broad range of radio-therapeutic agents, which include, but are not limited to, $^{61}$Co, $^{90}$Y, $^{106}$Rh, $^{149}$Nd, $^{150}$Pm, $^{188}$Re, and $^{212}$Bi.

These metal ions, in accordance with the preferred embodiment of the invention, are strongly bound to a chelator moiety of the second reagent immediately before administration into the patient. Thus, the active compound component remains stable in the system, thereby maximizing its effectiveness after delivery. However, the radioisotopes may also be bound to a chelator moiety of the second sequence-specific component in vivo.

The use of the chelator in accordance with the invention, reduces the non-specific background, which becomes important at the time when the cells are radioimaged, and minimizes the exposure of non-target tissues and organs to radioisotopes.

In order to guarantee specific targeting of chelated radioactive metals delivered using the method of the invention, the chelator molecule must exhibit the following properties:

(1) The chelator must exhibit a high binding affinity for the metal under consideration. This will ensure that the radioisotope is specifically bound to the conjugated protein at the position of the chelator molecules, rather than randomly associated with charged residues along the polynucleotide or polypeptide chain;

(2) The disassociation rate of the radioactive metals from the chelator molecule must be low in order to minimize the rate at which the radioactive metals become available for random binding to other non-specific proteins in vivo;

(3) The chelator must be capable of conjugation to the sequence-specific component of the second reagent under mild conditions, so as to avoid, or minimize inactivation of the second sequence-specific component; and (4) The presence of the chelator molecule in the reagent conjugate must not interfere with the function of the target recognition or sequence-specific components.

The preferred chelator for purposes of the instant invention is 1,2-diaminocyclohexanetetraacetate (DCTA), since this compound has a higher binding affinity than that of comparable chelators. Other chelators which are useful according to the invention are p-benzylamino-TETA (p-benzylamino 1,4, 8,11 tetra aza cyclohexyltetradecane, N, N', N'', N'''-tetra acetic acid) and its derivatives, as described by Moi et al. (1985) Analyt. Biochem. 148: 249; EDTA (ethylenediamine tetraacetic acid) and its derivatives, and DTPA (diethylenetriamine pentaacetic acid) as more fully set forth in U.S. Pat. No. 4,622,420 to Meares et. al. Other chelating groups can be used for purposes of the invention and are bonded to the metal ions through appropriate means.

In accordance with the preferred method of the invention, the chelator is attached to a linker arm before the linker is joined to the 3'-amino terminus of the oligonucleotide used as the sequence-specific component of the second reagent, as more fully described in U.S. Pat. Nos. 4,707,352, 4,767,609, and 4,772,548, as cited hereinabove and incorporated by reference herein.

Metal ions may be non-covalently bound to the chelator using procedures described in U.S. Pat. No. 4,707,352 as cited hereinabove. The chelated metal ions are separated from excess unchelated ions by column chromatography and administered after an appropriate time period and at an appropriate dosage, based upon the desired diagnostic or therapeutic use.

The method of the invention can be used in conjunction with any of the conventional imaging systems involving radioactivity, i.e. to detect gamma rays or X-rays. The preferred radionuclides useful for the invention emit positron or gamma rays. Thus, the most preferred metal ions useful in accordance with the invention include $^{111}$In, $^{68}$Ga, $^{55}$Co, and $^{61}$Cu. Emitted gamma rays may be detected using a variety of techniques. Positron emission tomography is the preferred method of radioimaging positrons in accordance with the invention. Any other available means of radioimaging radioactive compounds such as scintillography, may also be used in accordance with the invention.

The method of the invention has the additional advantage that only small amounts of the unbound active compound component remain in the system at the time of imaging, due, in part, to the complete specificity of the recognition and binding between the two sequence-specific components, as taught in the instant invention. Additionally, if there is any unbound active compound component, it may be cleared, in conjunction with the active compound component associated with the sequence-specific component, through the renal system prior to imaging. The incorporation of a clearance step into the procedure results in lower backgrounds, thereby yielding a clearer image when radioimaging is performed. In addition, any system can be tailored, based upon the instant invention, to detect or treat an unlimited range of targets, since one skilled in designing such systems can utilize an unlimited range of target recognition components, active compound components, and sequence-specific components for the purposes of the invention.

The present invention lends itself readily to the preparation of kits comprising one or more of the elements necessary to perform the intended diagnostic or therapeutic functions.

The examples which follow are set forth to illustrate various aspects of the present invention but are not intended to limit in any way its scope as more particularly set forth in the claims.

EXAMPLES

Preparation of Reagents

The target recognition component of the first reagent, which is comprised of an Fab' antibody fragment, is prepared by conventional methods from mouse ascites fluid containing HMB-45 monoclonal antibody (MA-930, Enzo Diagnostics, Inc.) which is specific for a surface cytoplasmic component of melanoma cells and embryonic melanocytes (Gown et al., "Monoclonal Antibodies to a Melanoma-Specific Cytoplasmic Antigen," United States-Canadian Division International Academy of Pathology, 74th Annual Meeting, Toronto, ONT, Mar. 11-15, 1985, *Laboratory Investigations* 52:25A-26A (1985).

According to their published abstract, Gown et al. developed a set of monoclonal antibodies (HMB-18, HMB-45, HMB-50) to a Triton-insoluble extract of human malignant melanoma cells. When screened on various cell lines in culture, it displays granular intracytoplasmic fluorescence only on melanoma cell lines and is nonreactive with all nonmelanoma tumor cell lines tested. Ultrastructural immunocytochemical studies show that the antibodies localize to premelanosomes. Gown et al. screened 26 cases of malignant melanoma metastatic to either subcutis, lung, or lymph node. Twenty-four of the 26 cases were positive with one or more of the monoclonal antibodies. Epithelioid melanoma cells displayed more uniform immunoreactivity than spindle cell variants. None of the 56 cases of carcinomas, 19 lymphomas, or 22 other sarcomas were positive with any of the three anti-melanoma antibodies. Intradermal nevus cells were generally nonreactive with these antibodies, although junctional or intradermal nevus cells displayed variable positivity. Interestingly, normal melanocytes were nonreactive. These antibodies work optimally in Camoy's- or alcohol-fixed, paraffin-embedded tissues, but standard formaldehyde-fixed, paraffin-embedded tissues can be used if pretreated with pronase. Thus, these three HMB monoclonal antibodies can be of great assistance to the surgical pathologist in distinguishing metastatic malignant melanomas from poorly differentiated carcinomas, sarcomas, and lymphomas.

The Fab' antibody fragment is then modified by the addition of a thiol group to facilitate linkage to the sequence-specific component of the reagent. This is accomplished either by reaction of the Fab' fragment with the Traut Reagent (Jue et al., "Addition of Sulfhydryl Groups to *Escherichia coli* Ribosomes by Protein Modication with 2-Iminothiolane(Methyl 4-Mercaptobutyrimidate)," *Biochemistry* 17:5399-5406 (1978)), or by treating the Fab' fragment according to the SPDP method (Carisson et al., "Protein Thiolation and Reversible Protein-Protein Conjugation," *Biochemical Journal* 173:723-727 (1978)).

In the aforementioned Jue et al. (1978) publication (page 5401), there is disclosed a reaction of 2-iminothiolane with $Nbs_2$. $Nbs_2$ titration is employed to test for sulfhydryl groups in freshly prepared solutions of 2-iminothiolane. When 2-iminothiolane is added to TEA buffer containing $Nbs_2$ at 7° C., there is no initial increase in absorbance at 412 nm as shown in FIG. 1 (figure not shown below), indicating the absence of free sulfhydryl groups. Addition of glycylglycine to the reaction (17.5 mM; about 180-fold excess over 2-iminothiolane) leads to the rapid appearance of sulfhydryl groups. Similar titrations at 25° C. showed that sulfhydryl groups are very slowly exposed in the absence of any primary amine. The initial rate of formation of sulfhydryl groups from 2-iminothiolane (at concentrations of 0.1 mM and 1.0 mM) in TEA buffer at 25° C. was 0.9% per min of the total sulfhydryl groups that are generated by addition of glycylglycine. This appearance of sulfhydryl groups in the absence of amines is almost undetectable at 7° C. (FIG. 1—not shown below).

The weight of 2-iminothiolane equivalent to 1 mol of free sulfhydryl groups released upon treatment with glycylglycine can be determined. The $Nbs_2$ titration procedure shown in FIG. 1 (figure not shown below) can be used.

In FIG. 1, the reaction of 2-iminothiolane with $Nbs_2$,2-iminothiolane (13 µg in 10 µL of a stock solution in acetonitrile) is added to 1.0 mL of TEA buffer, pH 8.0, containing 100 µL of 10 mM $Nbs_2$ at 7° C. The absorbance change at 412 nm is followed. After 10 min, glycylglycine (pH 8.0) is added to a final concentration of 17.5 mM. Using the aforementioned titration procedure of FIG. 1, the maximum absorbance change at 412 nm promoted by glycylglycine can be measured. Five determinations of the sulfhydryl group concentration derived from 2-iminothiolane (5.527 µg/mL) give values of 38.67, 39.55, 40.29, 40.29, and 40.66 µM. From these values, it is calculated that 138 g (±2 g) of 2-iminothiolane released 1 mol of free sulfhydryl group upon treatment with a primary amine.

Jue et al. further describe on page 5403 the reaction of 2-iminothiolane with amines in a subsection so titled. Conditions for controlling more precisely the extent of modification of ribosomes may be achieved by addition of excess amines to terminate the protein modification reaction by removal of 2-iminothiolane. The rate of reaction of 2-iminothiolane (0.1 mM) at pH 8.0 with various amines (20 mM) at 22° C. is shown in Table II (below). The reaction is monitored by measuring the rate of appearance of free sulfhydryl groups with $Nbs_2$ (FIG. 1 not shown). The evidence in Table II (below) shows that glycylglycine and glycinamide reacted rapidly with 2-iminothiolane, while Tris and ammonium only react slowly at rates barely greater than the rate of hydrolysis of the thiomidate. Tris is particularly unreactive even though the amine is at 200-fold molar excess over 2-iminothiolane. This results suggests that it is not necessary to carry out the modification reaction in triethanolamine buffers in the absence of Tris.

TABLE II

Reaction of 2-Iminothiolane with Amines at 22° C.$^a$

| amine | time for 50% reaction of 2-iminothiolane$^b$ (min) |
|---|---|
| no addition(hydrolysis) | 59.2 |
| glycylglycine | 1.6 |
| glycylglycine/$MgCl_2$ (1:1 mol/mol) | 1.5 |
| glycinamide | 1.6 |
| glycine | 3.5 |
| Tris | 45.3 |
| $NH_4Cl$ | 36.3 |

$^a$Amines (20 mM) from stock solutions (1.0 M), adjust to pH 8.0, were added to 2-iminothiolane (0.1 mM) in 50 mM-triethanolamine hydrochloride, pH 8.0, containing 1 mM $Nbs_2$.
$^b$Uncorrected for hydrolysis.

In the aforementioned Carlsson et al. publication, there is disclosed under the "Materials and Methods" section a series of syntheses and preparations. In this publication under the subsection titled "Synthesis of N-succinimidyl 3-(2-pyridyldithio)-propionate," beginning on page 724 and continuing through the first paragraph on page 725, a two-step procedure is performed. First, 3-mercapto-propionic acid is reacted by thiol-disulphide exchange with 2,2'-dipyridyl disulphide to give 2-carboxyethyl 2-pyridyl disulphide (Scheme 1a not shown below). This disulphide is then converted into N-succinimidyl 3-(2-pyridyldithio)propionate by esterification with N-hydroxysuccinimide by using NN'-dicyclohexylcarbodi-imide (Scheme 1b not shown below). The product of the first reaction, 2-carboxyethyl 2-pyridyl disulphide, can then undergo thiol-disulphide exchange with 3-mercaptopropionic acid (Scheme 1c not shown below) to form 2,2'-dicarboxyethyl disulphide. However, this side reaction is almost completely suppressed by using a 2-fold molar excess of 2,2'-dipyridyl disulphide.

Carlsson et al. disclose on page 725 the preparation of 2-carboxyethyl 2-pyridyl disulphide in a subsection so titled. 2,2'-Dipyridyl disulphide (3.75 g) is dissolved in 10 ml of ethanol (99.5%) and 0.4 ml of glacial acetic acid is added. The solution is stirred vigorously and 0.9 g of 3-mercaptopropionic acid in 5 ml of ethanol (99.5%) is added dropwise. The reaction mixture is left at 23° C. for 20 h. Ethanol is then removed by evaporation (Buchi Rotavapor at 10 mmHg pressure and at 40° C.). In the resulting pale-yellow oil there is a small amount of precipitate. This precipitate is removed by centrifugation after the oil is dissolved in a few milliliters of dichloromethane/ethanol (3:2, v/v) to 10 ml and then applied to a column (2 cm×24 cm) containing 75 ml of $Al_2O_3$ (equilibrated with dichloromethane/ethanol). The column is then eluted with the same solvent (dichloromethane/ethanol). T.l.c. on $Al_2O_3$ plates demonstrates that the main reaction product, 2-carboxyethyl 2-pyridyl disulphide, and also the by-product, 2,2'-dicarboxyethyl disulphide, adsorbs strongly on the $Al_2O_3$ under these conditions. 2,2'-Dipyridyl disulphide and pyridine-2-thione, however, moves with the solvent front. When all the yellow colour has been washed from the column (after about 150 ml of solvent) it is considered free from 2,2'-dipyridyl disulphide and pyridine-2-thione. This is also confirmed by t.l.c. of the eluate on $Al_2O_3$ plates with the same system and the reference substances pyridine-2-thione and 2,2'-dipyridyl disulphide.

The main product, 2-carboxyethyl 2-pyridyl disulphide, is then eluted with dichloromethane/ethanol (3:2, v/v) containing 4 ml of acetic acid/100 ml. Under these conditions the by-product 2,2'-dicarboxyethyl disulphide is retarded on the column and thus separated from the main product (confirmed by t.l.c. as described above). The fractions can be tested for the presence of 2-carboxyethyl 2-pyridyl disulphide by spectrophotometric determination of the 2-thiopyridone formed when 0.1 ml of the eluate is shaken with a few grains of dithiothreitol in 3 ml of $0.1M$-$NaHCO_3$ (lambdamax.=343 nm, epsilon=$8.08×10^3 M^{-1}.cm^{-1}$) (Grassetti & Murray, 1967; Stuchbury et al. 1975). The fractions containing 2-carboxyethyl 2-pyridyl disulphide are pooled and the solvent is removed by evaporation (at 10 mmHg and 30° C.). The resulting viscous oil, which has the odour of acetic acid, is redissolved in a small amount of dichloromethane/ethanol. The solvent is removed by evaporation. This procedure is repeated twice. Finally, the solvent is removed by exhaustive evaporation for 3 h at 23° C. by using an evaporator connected to an oil-pump (approx. 1 mmHg) and fitted with a cold-trap. The oil obtained, which no longer has the odour of acetic acid, is dissolved in 15 ml of dichloromethane. After addition of anhydrous MgSO4 the solution is kept in a sealed vessel at 23° C. The 2-carboxyethyl 2-pyridyl disulphide is not isolated. However, the yield based on 3-mercaptopropionic acid is found to be 40%. This is determined by measuring the pyridine-2-thione released on reduction of a small portion of the solution.

In the following section titled "Preparation of N-succinimidyl 3-(2-pyridyldithio)propionate), the dichloromethane solution of 2-carboxyethyl 2-pyridyl disulphide obtained as described above is filtered to remove $MgSO_4$. To the filtrate (15 ml) is added 0.439 of N-hydroxy-succinimide. The mixture is stirred vigorously for 20 min to dissolve most of the N-hydroxysuccinimide. Then, 0.789 of dicyclohexylcarbodiimide is added and the reaction is allowed to proceed at 23° C. (with occasional stirring) for 3 and one half h. The solution is dried with anhydrous $MgSO_4$, filtered, and the dichloromethane is removed by evaporation (Rotovapor at approx. 10 mmHg and 23° C.) to yield a pale-yellow oil containing a small amount of white precipitate. The oil is dissolved in cold (4° C.) dichloromethane and the solid material is (NN'-dicyclohexylurea) removed by filtration. The oil remaining after evaporating the solvent is dissolved in the smallest possible volume of ethanol (approx. 10 ml) and the solution is cooled to −20° C. The white crystals formed are filtered off and recrystallized from ethanol. The final product is then isolated by filtration and subsequently dried over anhydrous $P_2O_5$ for 24 h.

The product is found to be analytically pure N-succinimidyl 3-(2-pyridyldithio)propionate (see below). The yield from the two steps, based on 3-mercaptopropionic acid, is 30% (m.p. 78.5-80.5° C.) (Found: C, 46.19; H, 3.88; N, 8.96; S, 20.02. $C_{12}H_{12}O_4N_2S_2$ requires C, 46.14; H, 3.88; N, 8.97; S, 20.53%), delta (p.p.m.) (tetramethylsilane) 2.83 (4H, s, succinimidyl H), 3.12 (4H, s, —$CH_2$—$CH_2$—) and 6.90-8.82 (4H, m, pyridyl H).

In the next subsection titled "Introduction of 2-pyridyl disulphide structures into proteins by N-succinimidyl 3-(2-pyridyldithio)-propionate," the protein (0.05-2 μmol) is chromatographed on a Sephadex G-25 column with 0.1 M-sodium phosphate buffer containing 0.1 M—NaCl, pH 7.5, as eluent. (This is required to remove low-molecular-weight material that might react competitively with the reagent). The fraction collected in the void volume is adjusted to a volume of 2 ml with the buffer and, depending on the degree of substitution desired (i.e. mol of 2-pyridyl disulphide structures/mol of protein), 0.01-0.3 ml of N-succinimidyl 3-(2-pyridyldithio) propionate (20 mM in 99.5% ethanol) is added dropwise to the stirred protein solution. The reaction mixture is left for about 30 min at 23° C. Excess of reagent is then removed by gel filtration on Sephadex G-25. The content of 2-piridyl disulphide structures in the modified proteins is determined by adding 0.1 ml of 50 mM-dithiothreitol in distilled water to a properly diluted protein solution (2.0 ml). This treatment effects the release of pyridine-2-thione, which has a molar absorptivity of $8.08×10^3$ at 343 nm (Stuchbury et al., 1975). The amount of pyridine-2-thione released is equivalent to the content of 2-pyridyl disulphide groups in the protein. Since the 2-pyridyl disulphide group has its own absorbance at 280 nm (Grassetti & Murray, 1967) an erroneously high protein concentration will be obtained when calculated on the basis of absorbance at 280 nm. The additional absorbance can be allowed for by subtracting the $A_{280}$ contribution of the 2-pyridyl disulphide group from the total $A_{280}$ [as calculated by using the following expression: (concentration of 2-thiopyridone released on reduction)×5100=$A_{280}$ due to 2-pyridyl sulphide group (J. Carlsson and H. Drevin, unpublished work)]. In the case of large proteins with a low degree of substitution (1-2 mol of 2-pyridyl disulphide groups/mol of protein) the error, however, is not significant. The modified proteins is stored dissolved in 0.1M-sodium phosphate buffer/0.1M—NaCl, pH 7.5, at 4° C.

In the next section titled "Thiolation of proteins by N-succinimidyl 3-(2-pyridyldithio)propionate," 2-Pyridyl disulphide groups are introduced into the protein by N-succinimidyl 3-(2-pyridyldithio)propionate as described above. The molar excess of reagent ([reagent]/[protein] ratio) is chosen to give the desired degree of substitution (see Table 2).

TABLE 2

Introduction of 2-pyridyl disulphide groups into proteins by N-succinimidyl 3-(2-pyridyldithio)propionate and subsequent thiolation by specific reduction.

The protein (0.05-2 μmol) is dissolved in 0.1 M-sodium phosphate buffer/0.1 M-NaCl, pH 7.5 (2 ml). An ethanol solution (0.01-0.03 ml) of N-succinimidyl 3-(2-pyridyldithio)propionate (20 mM) is added in portions to the stirred protein solution and the reaction proceeds for 30 min at 23° C. Excess of reagent and low-molecular-weight reaction products are removed by gel filtration on Sephadex G-25. The numbers of 2-pyridyl disulphide structures introduced are calculated from the amount of pyridine-2-thione (molar absorptivity $8.08 × 10^3$ at $lambda_{max}$. 343 nm) released on treatment of the modified protein with a large excess of low-molecular-weight thiol compound (e.g. dithiothreitol). Thiolation of protein is performed by a two-step procedure. First, 2-pyridyl disulphide structures are introduced as described above. The protein-bound 2-pyridyl disulphide groups are then converted into protein-bound thiol groups by TABLE 2-continued specific reduction with dithiothreitol (25 mM) at pH 4.5 for 30 min. Blank experiments with the native proteins show that this treatment does not lead to reduction of native disulphide bonds. After removal of excess of dithiothreitol and pyridine-2-thione by gel filtration on Sephadex G-25, the number of protein-bound thiol groups is estimated by reaction with 2,2'-dipyridyl disulphide (Grassetti & Murray, 1967). Abbreviation: Py-2-S—S,2-pyridyl disulphide group; epsilon, epsilon-amino; alpha, alpha-amino group.

| Protein | Mol of amine group/mol of protein | Amount of reagent in aminolysis reaction ([reagent]/[protein]) | Degree of substitution obtained (mol of Py-2-S—S/mol of protein) | Protein-thiol groups detected after specific reduction of protein bound Py-2-S—S structures by dithiothreitol (mol of thiol group/mol of protein) |
| --- | --- | --- | --- | --- |
| Ribonuclease A (bovine) | 10(epsilon), 1(alpha)* | 1 | 0.8 | 0.75 |
|  |  | 2.4 | 2.1 | — |
|  |  | 5.5 | 3.0 | — |
|  |  | 5.7 | 3.2 | — |
| alpha-amylase (bacterial) | 18(epsilon), 1(alpha)+ | 1.5 | 1.0 | 0.95 |
|  |  | 9 | 3.0 | 2.3 |
| gamma-Globulin (bovine) | 50-70 (epsilon), 4(alpha)# | 3 | 2.3 | 1.7 |
|  |  | 10 | 3.3 | — |
| Rabbit anti-(human transferrin) antibodies | 59(epsilon), 3(alpha)# | 2 | 1.7 | 1.3 |
|  |  | 2.5 | 1.7 | — |
|  |  | 3.5 | 2.7 | — |
| Peroxidase (horseradish) | 4§ | 4.8 | 0.5 | — |
|  |  | 9.6 | 0.7 | — |
|  |  | 25.0 | 2.3 | — |

*Dayhoff (1972).
+Junge et al. (1959).
Cohen & Porter (1964).
§Klapper & Hackett (1965)

The protein-2-pyridyl disulphide derivative is then transferred to sodium acetate buffer, pH 4.5, containing 0.1M—NaCl, by dialysis or gel filtration. Dithiothreitol dissolved in a small volume of the acetate buffer mentioned above is then added to a final concentration of 25 mM. This treatment effects the reduction of the protein-bound 2-pyridyl disulphide bonds without concomitant reduction of native protein disulphide bonds. In the case of proteins lacking native disulphide bonds, e.g. alpha-amylase, the reduction can of course be performed at alkaline pH with a large excess of dithiothreitol or other low-molecular-weight thiol compounds. After treatment for 30-40 min the thiolated protein is separated from the low-molecular-weight material by gel filtration on Sephadex G-25. The thiol content of the protein is estimated by reaction with 2,2'-dipyridyl disulphide (Grassetti & Murray, 1967; Stuchbury et al., 1975).

Since the thiol group is very reactive and can take part in unwanted reactions it is recommended that the modified protein be stored in the pyridyl disulphide form and be reduced just before the protein thiol is used.

Carlsson et al. also disclose the preparation of protein-protein conjugates by N-succinimidyl 3-(2-pyridyldithio) propionate in a subsection so named on page 726 The technique described in this subsection should be applicable to all proteins containing amino groups that are reactive toward N-succinimidyl 3-(2-pyridyldithio)propionate. To demonstrate the method alpha-amylase is bonded to urease, ribonuclease to bovine mercaptalbumin and peroxidase to rabbin anti-(human transferrin) antibodies.

In the next subsection titled "Preparation of ribonuclease-mercaptalbumin conjugate," bovine serum albumin (80 mg or 1.200 nmol containing 490 nmol of mercaptoalbumin) is dissolved in 1.95 ml of 0.1M-sodium phosphate buffer, pH7.5, containing 0.1M—NaCl. Ribonuclease is treated with N-succinimidyl 3-(2-pyridyldithio)-propionate as described above to give a derivative containing 2.1 mol of 2-pyridyl disulphide groups/mol of enzyme. This derivative (6.9 mg; 500 nmol) in 0.5 ml of 0.1M-sodium phosphate buffer, pH7.5, containing 0.1M—NaCl is mixed with the albumin solution. The reaction is followed by measuring the pyridine-2-thione released as a result of the thiol-disulphide exchange reaction. After 40 min, when the reaction is almost complete as judged from the amount of pyridine-2-thione released, the reaction mixture is gel-filtered on a Sepharose 6B column (2 cm×63 cm) with 0.3M-NaCl as the medium. The u.v.-absorbance and ribonuclease activity of the fractions are determined.

As a control, a mixture of native ribonuclease (6.9 mg) and native albumin (80 mg) in 2.5 ml of 0.1M-phosphate buffer, pH7.5, containing 0.1M—NaCl is also gel-filtered on a Sepharose 6B column to determine whether any conjugate held together by non-covalent bonds is formed. To one of the fractions containing ribonuclease-albumin conjugate (1.0 ml) is added solid urea and 2-mercaptoethanol to give final concentrations of 8M and 0.45M respectively. The solution is adjusted to pH8 by addition of 2M—-NaOH. Under these conditions ribonuclease is completely reduced (White, 1972a). After 2h at 23° C. the mixture is gel-filtered on a Sephadex G-75 column in 0.1M-Tris/HCl buffer, pH8.5, containing 0.3M—NaCl. The $A_{280}$ of the fractions is determined. The fractions are left standing at about 23° C. for 3 h to allow the ribonuclease to reoxidize (White, 1972a). Thereafter the fractions are adjusted to pH7 and the ribonuclease activity is determined as described later under the subsection titled "Enzyme activity measurements." The activity of this enzyme (ribonuclease activity) towards cytidine 2':3'-cyclic monophosphoric acid (38 mM) is determined titrimetrically as described by Axen et al. (1971). The assay pH is 7.0, which is optimal for both native and conjugated ribonuclease.

An oligonucleotide, 20 bases in length, comprised of 2'-chloro-deoxyguanosine bases, acts as the sequence-specific component of the first reagent. This oligonucleotide is prepared on an automated oligonucleotide synthesizer using phosphoramidite chemistry. A primary amino group is introduced at the 3'-terminus of the oligonucleotide during its synthesis using the reagent 3'Amine O CPG (Clontech Laboratories, Inc., Palo Alto, Calif.). The primary amine at the 3'-terminus of the oligonucleotide is then reacted with SIAB (succinimydl 4-iodoacetyl aminobenzoate, Pierce, Rockford, Ill.) to introduce an iodoacetamide residue, according to Weltman, et al. (Weltman, J. K., et al., "N-Succinimidyl(4-lodoacetyl)Aminobenzoate: A New Heterobifunctional Crosslinker," *Biotechniques* 1:148-152 (1983)). Weltman et al. disclose in their "MATERIALS AND METHODS" section the preparation of N-succinimidyl(4-iodoacetyl)aminobenzoate (SIAB). SIAB is prepared as outlined in FIG. 1 of Weltman et al. (figure not shown below). Iodoacetic anhydride, 354 mg (1 mmole) purchased from ICN Pharmaceuticals-K and K Laboratories, is reacted with 68.6 mg (0.5 mmoles) of p-aminobenzoic acid in 7.5 ml of dioxane, for 5 hours at room temperature in the dark, and then for 2 days at 4 degrees. A white flocculent intermediate (4-iodoacetylaminobenzoic acid) is isolated by centrifugation and triturated with 0.5 ml of diethyl ether three times. The resulting white intermediate is dried with hot air with a yield of 160 mg.

Dicyclohexycarboiimide (86.2 mg; 0.4 mmoles) is added to a solution of the intermediate (128 mg; 0.4 mmoles) and N-hydroxysuccinimide (48.5 mg; 0.4 mmoles) in 3.35 ml of tetrahydrofuran (THF) and placed at 4 degrees for 20 hours. A precipitate is removed and the supernatant liquid is recovered and evaporated to dryness and triturated with diethyl ether. Pale yellow crystals of SIAB are recovered, yield 135 mg (80%), melting point 172-175 degrees. The yellow crystals of SIAB are recrystallized from methanol and washed twice with diethyl ether, yielding white crystals of SIAB, melting point 194-196 degrees with decomposition. The calculated molecular weight of SIAB is 402 daltons. The iodoacetamide-derivatized oligo(dG) is then reacted with the thiol group on the derivatized Fab' fragment, thereby forming the first reagent of the invention.

The second reagent is comprised of the beta emitter $^{90}$Y, as the active compound component, and the chelating moiety 1,2-diaminocyclohexanetetraacetate (DCTA) connected to the allylamino residues on a 20 base long oligonucleotide with the sequence [(2'-chloro-deoxycytosine)$_3$ (2'-chloro-deoxycytosine-5-allylamine)]$_5$ as the sequence-specific component of the second reagent, as described in U.S. Pat. Nos. 4,707,352, 4,767,609 and 4,772,548, as cited hereinabove. The beta emitter, $^{90}$Y, which is cytotoxic, is attached to the chelator moiety of the conjugate, in accordance with U.S. Pat. No. 4,707,352, to yield the second reagent.

Therapeutic Application of Reagents

A solution containing 2.5 µg/ml of the first reagent in a 0.9% sodium chloride solution, prepared as described above, is administered to a patient intravenously at a dose of 15-20 µg/kg body weight over a three hour period. An equilibration period of 1-3 days is required for the antibody fragments in the first reagent to achieve maximal localization on the tumors. At the end of this period, all or most of the first reagent circulating in the blood is cleared to prevent it from binding to the second reagent. This clearance is effected either by a reagent similar to the second reagent. i.e., one in which the active compound in the second reagent is replaced with human transferrin, or by a reagent which is comprised of target analyte or target analyte analogs linked to transferrin. Transferrin is a slowly diffusible serum protein which will selectively clear excess reagents in the blood, rather than target analyte-bound reagents, if it is administered a short time before the addition of the active compound component of the second reagent. This clearing compound is administered intravenously at a dose of 0.1-0.4 nmol/kg body weight. One to three hours later, 0.001-0.01 nmol/kg body weight of $^{90}$Y is loaded onto the chelator moiety attached to the 2'-chloro-deoxycytosine-containing oligonucleotide to form the second reagent, as disclosed in U.S. Pat. No. 4,707,352 cited hereinabove. The second reagent is purified from excess, unchelated metal ions by column chromatography and is administered to the patient intravenously within 30 minutes of its preparation. The 2'-chloro-deoxycytosine-containing oligonucleotide in the second reagent rapidly finds and binds to its complementary 2'-chloro-deoxyguanosine-containing oligonucleotide in the first reagent which is attached to the tumor-bound antibody. The cytotoxic effect of the $^{90}$Y results in tumor cell death.

Radioimaging Applications

Reagents and methods identical to those described above, with the exception that the active compound component of the second reagent is the positron emitter $^{68}$Ga, may be used for diagnostic purposes. Tumors may be imaged by positron emission tomography, or by any other appropriate imaging techniques, 2-3 hours after the $^{68}$Ga has been administered to the patient.

Equivalents

Those skilled in the art will recognize or be able to ascertain, using no more than routine experimentation, many equivalents to the specific embodiments of the invention described herein. Such equivalents are intended to be encompassed by the following claims.

Modifications of the above described modes for carrying out the invention that are obvious to those skilled in radiochemistry, radioimaging, and related fields are intended to be within the scope of the following claims.

We claim:

1. A method for visualizing specific target analytes in a subject which comprises:
   (1) providing a reagent conjugate useful for delivering active compounds to specific target analytes into a subject, said conjugate comprising
      (a) a first reagent comprising a specific target recognition component which comprises a Fab' antibody fragment which is covalently attached to a first sequence-specific component comprising a first oligonucleotide comprised of 2'-chlorodeoxy-guanosine which is about 20 bases long; and
      (b) a second reagent comprising an active compound component linked to a second sequence-specific component which specifically recognizes and binds to said first sequence-specific component, said second reagent-comprised of $^{90}$y bound to a 1,2-diaminocyclohexane-tetraacetate (DCTA) chelating moiety, said second sequence-specific component comprising a second oligonucleotide, said DCTA chelating moiety being covalently attached through the allylamino group at the 5-position of a cytidyl residue in said second oligonucleotide which comprises the sequence [(2'-chloro-deoxycytosine)$_3$(2'-chloro-deoxycytosine-5-allylamine)]$_5$, and
   wherein said first and second sequence-specific components (a) and (b) have been rendered nuclease resistant by the presence of one or more nucleotide analogs to said oligonucleotides;
   (2) introducing into said subject an effective amount of said reagent conjugate; and
   (3) visualizing said specific target analytes.

2. The method of claim 1, wherein said introducing step 2) is carried out by an administration means comprising intramuscular, intrabronchial, intrapleural, intraperitoneal, intraarterial, lymphatic, intravenous, subcutaneous, cerebrospinal, or combinations thereof.

3. The method of claim 1, wherein said target analytes comprise low or high molecular weight molecules, molecular complexes or cell surface components, and combinations thereof.

4. The method of claim 1, wherein said target analytes comprise biological systems or parts thereof which comprise abnormal eukaryotic cells, cells with proteins not generally found on cell surfaces, cells with proteins found only at a defined stage on the life cycle of the organism, or pathogenic components of cells, tissues, and organs, and combinations thereof.

5. The method of claim 4, wherein said abnormal eukaryotic cells comprise cancer cells.

6. The method of claim 1, wherein said target analytes comprise biological systems selected from cells, tissues and organs bearing cell surface epitopes, or combinations thereof.

7. The method of claim 6, wherein said cells, tissues or organs bearing cell surface epitopes are located in a lymph node, an inflammation, a tumor, or an abscess in said subject.

8. A method for delivering active compound components to specific target analytes in a subject which comprises:
(1) providing:
   (a) a first reagent comprising a specific target recognition component which comprises a Fab' antibody fragment which is covalently attached to a first sequence-specific component comprising a first oligonucleotide comprised of 2'-chlorodeoxy-guanosine which is about 20 bases long; and
   (b) a second reagent comprising an active compound component linked to a second sequence-specific component which specifically recognizes and binds to said first sequence-specific component, said second reagent comprised of $^{90}$y bound to a 1,2-diaminocyclohexane-tetraacetate (DCTA) chelating moiety, said second sequence-specific component comprising a second oligonucleotide, said DCTA chelating moiety being covalently attached through the allylamino group at the 5-position of a cytidyl residue in said second oligonucleotide which comprises the sequence [(2'-chloro-deoxycytosine)$_3$ (2'-chloro-deoxycytosine-5-allylamine)]$_5$;
   wherein said first and second sequence-specific components (a) and (b) have been rendered nuclease resistant by the presence of one or more nucleotide analogs to said oligonucleotides;
(2) introducing into said subject an effective amount of said first reagent;
(3) allowing said first reagent to equilibrate to achieve sufficiently maximal localization on said specific targets analytes;
(4) introducing into said subject an effective amount of said second reagent; and
(5) allowing said second reagent to bind to said first reagent, thereby delivering said active compound components to the specific target analytes in said subject.

9. The method of claim 8, wherein said introducing step (2) is carried out by an administration means comprising intramuscular, intrabronchial, intrapleural, intraperitoneal, intraarterial, lymphatic, intravenous, subcutaneous, cerebrospinal, or combinations thereof.

10. The method of claim 8, wherein any of said first reagent that is unbound to said target analyte is cleared from the subject's circulatory system by administering to said subject a clearing agent following step (3).

11. The method of claim 8, wherein said target recognition component of the first reagent is introduced and allowed to equilibrate on said target analytes prior to the introduction and binding of said first sequence specific component, thereby forming said first reagent in vivo.

12. The method of claim 8, wherein said second sequence-specific component is introduced and allowed to bind to said first sequence-specific component following step (3) and prior to the introduction and binding of said active compound component, thereby forming said second reagent in vivo.

13. The method of claim 8, wherein said target analytes comprise biological systems or parts thereof which comprise abnormal eukaryotic cells, cells with proteins not generally found on cell surfaces, cells with proteins found only at a defined stage on the life cycle of the organism, or pathogenic components of cells, tissues, and organs, and combinations thereof.

14. The method of claim 13, wherein said abnormal eukaryotic cells comprise cancer cells.

* * * * *